US009227053B2

(12) United States Patent
Bonde et al.

(10) Patent No.: US 9,227,053 B2
(45) Date of Patent: Jan. 5, 2016

(54) SELF EXPANDING ELECTRODE CUFF

(75) Inventors: Eric H. Bonde, Minnetonka, MN (US);
Roy L. Testerman, New Hope, MN (US); Timothy P. Herbert, Maple Grove, MN (US); Mark A. Christopherson, Shoreview, MN (US); Jesse D. Geroy, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 986 days.

(21) Appl. No.: 12/990,702

(22) PCT Filed: May 1, 2009

(86) PCT No.: PCT/US2009/042539
§ 371 (c)(1),
(2), (4) Date: Mar. 8, 2011

(87) PCT Pub. No.: WO2009/135138
PCT Pub. Date: Nov. 5, 2009

(65) Prior Publication Data
US 2011/0147046 A1    Jun. 23, 2011

Related U.S. Application Data

(60) Provisional application No. 61/049,927, filed on May 2, 2008.

(51) Int. Cl.
*A61N 1/18* (2006.01)
*A61N 1/05* (2006.01)

(52) U.S. Cl.
CPC ............ *A61N 1/0556* (2013.01); *A61N 1/0558* (2013.01); *A61N 1/05* (2013.01); *A61N 1/0526* (2013.01)

(58) Field of Classification Search
CPC . A61N 1/0556; A61N 1/0558; A61N 1/0526; A61N 1/05; A61B 5/6884
USPC .................................................. 607/115–119
See application file for complete search history.

(56) References Cited

U.S. PATENT DOCUMENTS

| 3,654,933 A | 4/1972 | Hagfors |
| 3,774,618 A | 11/1973 | Avery |
| 4,379,462 A | 4/1983 | Borkan |
| 4,512,351 A | 4/1985 | Pohndorf |

(Continued)

FOREIGN PATENT DOCUMENTS

| EP | 0865800 | 9/1998 |
| JP | 2002017872 | 1/2002 |

(Continued)

OTHER PUBLICATIONS

Sahin, Durand, and Haxhiu. "Chronic recordings of hypoglossal nerve activity in a dog model of upper airway obstruction." Journal of Applied Physiology 87(6). 1999. pp. 2197-2206.*

(Continued)

*Primary Examiner* — Christopher D Koharski
*Assistant Examiner* — Pamela M Bays
(74) *Attorney, Agent, or Firm* — Dicke, Billig & Czaja, PLLC

(57) ABSTRACT

An electrode lead assembly is described. The lead assembly includes an expandable cuff electrode that includes a series of spaced apart electrode elements and a substantially re-closable opening.

28 Claims, 12 Drawing Sheets

(56) References Cited

U.S. PATENT DOCUMENTS

| | | | |
|---|---|---|---|
| 4,573,481 A | 3/1986 | Bullara et al. | |
| 4,590,946 A | 5/1986 | Loeb | |
| 4,602,624 A | 7/1986 | Naples et al. | |
| 4,628,614 A | 12/1986 | Thompson | |
| 4,649,936 A | 3/1987 | Ungar et al. | |
| 4,940,065 A | 7/1990 | Tanagho et al. | |
| 4,967,755 A | 11/1990 | Pohndorf | |
| 5,038,781 A | 8/1991 | Lynch | |
| 5,158,080 A | 10/1992 | Kallok | |
| 5,238,006 A | 8/1993 | Markowitz | |
| 5,265,624 A | 11/1993 | Bowman | |
| 5,282,468 A | 2/1994 | Klepinski | |
| 5,324,322 A | 6/1994 | Grill, Jr. et al. | |
| 5,344,438 A | 9/1994 | Testerman | |
| 5,351,394 A | 10/1994 | Weinberg | |
| 5,398,596 A | 3/1995 | Fond | |
| 5,400,784 A | 3/1995 | Durand et al. | |
| 5,487,756 A | 1/1996 | Kallesoe et al. | |
| 5,505,201 A | 4/1996 | Grill, Jr. et al. | |
| 5,531,778 A | 7/1996 | Maschino | |
| 5,591,216 A | 1/1997 | Testerman et al. | |
| 5,634,462 A | 6/1997 | Tyler et al. | |
| 5,741,319 A | 4/1998 | Woloszko et al. | |
| 5,824,027 A | 10/1998 | Hoffer et al. | |
| 5,919,220 A | 7/1999 | Stieglitz | |
| 5,938,596 A * | 8/1999 | Woloszko | A61N 1/05 600/377 |
| 6,093,197 A | 7/2000 | Bakula et al. | |
| 6,366,815 B1 | 4/2002 | Haugland | |
| 6,456,866 B1 | 9/2002 | Tyler et al. | |
| 6,587,725 B1 | 7/2003 | Durand et al. | |
| 6,600,956 B2 | 7/2003 | Maschino | |
| 6,907,293 B2 | 6/2005 | Grill | |
| 6,907,295 B2 | 6/2005 | Gross | |
| 7,054,692 B1 | 5/2006 | Whitehurst et al. | |
| 7,065,410 B2 | 6/2006 | Bardy | |
| 7,082,336 B2 | 7/2006 | Ransbury et al. | |
| 7,248,930 B1 | 7/2007 | Woloszko et al. | |
| 7,389,149 B2 | 6/2008 | Rossing et al. | |
| 7,395,119 B2 | 7/2008 | Hagen et al. | |
| 7,463,934 B2 | 12/2008 | Tronnes et al. | |
| 7,468,039 B2 * | 12/2008 | Lui | A61B 5/0261 128/100.1 |
| 7,499,742 B2 | 3/2009 | Bolea et al. | |
| 7,596,414 B2 | 9/2009 | Whitehurst | |
| 7,630,771 B2 | 12/2009 | Cauller | |
| 7,634,315 B2 | 12/2009 | Cholette | |
| 7,644,714 B2 | 1/2010 | Atkinson et al. | |
| 7,680,538 B2 | 3/2010 | Durand et al. | |
| 7,725,195 B2 | 5/2010 | Lima et al. | |
| 7,787,959 B1 | 8/2010 | Morgan | |
| 7,809,442 B2 | 10/2010 | Bolea et al. | |
| 7,996,092 B2 * | 8/2011 | Mrva | A61N 1/0526 607/118 |
| 8,155,757 B1 * | 4/2012 | Neisz | A61N 1/0556 607/118 |
| 2003/0040785 A1 * | 2/2003 | Maschino et al. | 607/118 |
| 2004/0111139 A1 | 6/2004 | McCreery | |
| 2005/0010265 A1 | 1/2005 | Baru Fassio et al. | |
| 2006/0030919 A1 * | 2/2006 | Mrva et al. | 607/118 |
| 2006/0103407 A1 | 5/2006 | Kakizawa et al. | |
| 2006/0195170 A1 | 8/2006 | Cohen | |
| 2006/0266369 A1 | 11/2006 | Atkinson et al. | |
| 2006/0271137 A1 | 11/2006 | Stanton-Hicks | |
| 2006/0282127 A1 | 12/2006 | Zealear | |
| 2007/0043411 A1 | 2/2007 | Foster | |
| 2007/0129780 A1 | 6/2007 | Whitehurst et al. | |
| 2007/0233204 A1 | 10/2007 | Lima et al. | |
| 2007/0239243 A1 | 10/2007 | Moffitt et al. | |
| 2007/0255379 A1 | 11/2007 | Williams et al. | |
| 2008/0046055 A1 | 2/2008 | Durand et al. | |
| 2008/0091255 A1 | 4/2008 | Caparso et al. | |
| 2008/0103545 A1 | 5/2008 | Bolea et al. | |
| 2008/0103570 A1 | 5/2008 | Gerber | |
| 2008/0132987 A1 | 6/2008 | Westlund et al. | |
| 2008/0172101 A1 | 7/2008 | Bolea et al. | |
| 2008/0172116 A1 | 7/2008 | Mrva et al. | |
| 2008/0177348 A1 | 7/2008 | Bolea et al. | |
| 2008/0319506 A1 | 12/2008 | Cauller | |
| 2009/0099439 A1 | 4/2009 | Barolat | |
| 2009/0210042 A1 | 8/2009 | Kowalczewski | |
| 2010/0047376 A1 | 2/2010 | Imbeau | |
| 2010/0094379 A1 | 4/2010 | Meadows et al. | |
| 2010/0145221 A1 | 6/2010 | Brunnett et al. | |
| 2010/0174341 A1 | 7/2010 | Bolea et al. | |
| 2010/0198103 A1 | 8/2010 | Meadows et al. | |
| 2010/0241195 A1 | 9/2010 | Meadows et al. | |
| 2010/0241207 A1 | 9/2010 | Bluger | |
| 2011/0093036 A1 | 4/2011 | Mashiach | |
| 2011/0152965 A1 | 6/2011 | Mashiach | |

FOREIGN PATENT DOCUMENTS

| | | | |
|---|---|---|---|
| JP | 2003220420 | 8/2003 | |
| WO | 2007140597 | 12/2007 | |
| WO | 2008025155 | 3/2008 | |
| WO | 2008048471 | 4/2008 | |
| WO | WO 2008/048471 | * 4/2008 | A61M 16/00 |
| WO | 2009048580 | 2/2009 | |
| WO | 2009048581 | 4/2009 | |
| WO | 2009135138 | 11/2009 | |
| WO | 2009135140 | 11/2009 | |
| WO | 2009135142 | 11/2009 | |
| WO | 2009140636 | 11/2009 | |
| WO | 2010039853 | 4/2010 | |
| WO | 2010059839 | 5/2010 | |
| WO | 2010117810 | 10/2010 | |

OTHER PUBLICATIONS

Eisele Article—David W. Eisele, MD et al., "Tongue neuromuscular and direct hypoglossal nerve stimulation for obstructive sleep apnea," Otolaryngologic Clinics of North America, Otolayngol Clin N Am 36 (2003) 501-510 (10 pages).

Goodall Article—Eleanor V. Goodhall et al., "Position-Selective Activation of Peripheral Nerve Fibers with a Cuff Electrode," IEEE Transaction on Biomedical Engineering, vol. 43, No. 8, Aug. 1996, pp. 851-856.

Naples Article—Gregory G. Naples et al., "A Spiral Nerve Cuff Electrode for Peripheral Nerve Stimulation," 8088 IEEE Transactions on Biomedical Engineering, 35. Nov. 1988, No. 11, New York, NY, pp. 905-915.

Oliven Article—Arie Oliven et al., "Upper airway response to electrical stimulation of the genioglossus in obstructive sleep apnea," Journal of Applied Physiology, vol. 95, pp. 2023-2029, Nov. 2003, www.jap.physiology.org on Sep. 18, 2006. (8 pages).

Schwartz Article—Alan R. Schwartz MD et al., Theraputic Electrical Stimulation of the Hypoglossal Nerve in Obstructive Sleep Apnea, Arch Otolaryngol Headand Neck Surg., vol. 127, Oct. 2001, pp. 1216-1223. Copyright 2001 American Medical Association. (8 pages).

Park Article—Jung I. Park MD, PhD, "Preoperative Percutaneous Cranial Nerve Mapping in Head and Neck Surgery", American Medical Association, 2003, (6 pages).

* cited by examiner

SELF EXPANDING ELECTRODE CUFF

CROSS-REFERENCE TO RELATED APPLICATIONS

This Utility patent application claims the benefit of International Application No. PCT/US2009/042539, filed May 1, 2009, which claims the benefit of U.S. Provisional Patent Application No. 61/049,927, filed May 2, 2008, both of which are incorporated herein by reference.

TECHNICAL FIELD

The invention relates generally to an implantable stimulation system for stimulating and monitoring soft tissue in a patient, and more particularly, the invention relates to an expandable electrode cuff for positioning an electrode of an implantable stimulation system about a nerve for stimulation and/or monitoring of nerve tissue.

BACKGROUND

Sleep apnea generally refers to the cessation of breathing during sleep. One type of sleep apnea, referred to as obstructive sleep apnea (OSA), is characterized by repetitive pauses in breathing during sleep due to the obstruction and/or collapse of the upper airway, and is usually accompanied by a reduction in blood oxygenation saturation.

One treatment for obstructive sleep apnea has included the delivery of electrical stimulation to the hypoglossal nerve, located in the neck region under the chin. Such stimulation therapy activates the upper airway muscles to maintain upper airway patency. In treatment of sleep apnea, increased respiratory effort resulting from the difficulty in breathing through an obstructed airway is avoided by synchronized stimulation of an upper airway muscle or muscle group that holds the airway open during the inspiratory phase of breathing. For example, the genioglossus muscle is stimulated during treatment of sleep apnea by a cuff electrode place around the hypoglossal nerve.

Because of the significant amount of movement in multiple directions that can take place under the chin, positioning an electrode to enable stimulation of the hypoglossal nerve becomes a significant challenge. On the one hand, placement of the electrode and lead in close proximity to the hypoglossal nerve can result in irritation to the nerve as a result of normal motion of the chin and neck, while on the other hand, without close adherence to the nerve, buildup of connective tissue between the nerve and the electrode cuff and lead can occur, causing low thresholds, thereby reducing the effectiveness of the delivered stimulation by the device.

Another challenge in placing an electrode for nerve stimulation therapy relates to the tendency of the hypoglossal nerve to swell because the nerve is disturbed while manipulating the nerve to implant the cuff electrode and/or while securing the cuff electrode about the nerve. Once the cuff electrode secured on the nerve, swelling of the nerve can result in excess pressure on the nerve by the electrode and lead. In addition, once the electrode has initially been implanted, fibrosis tends to cause the location of the electrode to become more fixed. Therefore, during the first month following the implant of the lead and electrode, it is desirable to keep the electrode cuff properly positioned on the nerve, while at the same time not placing undue pressure on a swelling nerve. An additional challenge in placing the electrode for nerve stimulation results from the fact that stimulation currents should be confined to the hypoglossal nerve in order to prevent other nearby nerves or muscles from being stimulated, which would result in patient discomfort and loss of sleep.

BRIEF DESCRIPTION OF THE DRAWINGS

Aspects and features of the present invention will be appreciated as the same becomes better understood by reference to the following detailed description of the embodiments of the present disclosure when considered in connection with the accompanying drawings, wherein.

DESCRIPTION OF EMBODIMENTS

The following detailed description is merely exemplary in nature and is not intended to limit the present disclosure or the application and uses of the embodiments of the present disclosure. Furthermore, there is no intention to be bound by any expressed or implied theory presented in the preceding technical field, background, brief summary or the following detailed description.

Embodiments of the present disclosure provide an electrode cuff that, once engaged about a nerve via a re-closable opening, is automatically expandable to accommodate increases in the diameter of a nerve while still maintaining contact between electrodes of the cuff against the nerve. Among other features to be described, the electrode cuff includes a combination of opposed and/or overlapping flange members that are biased to remain in releasable contact with each other, and slidable movable relative to each other, to provide the automatic expandability without losing closure of the nerve within the electrode cuff.

These embodiments, and other embodiments, will be described in association with FIGS. 1-21.

Figure 1:
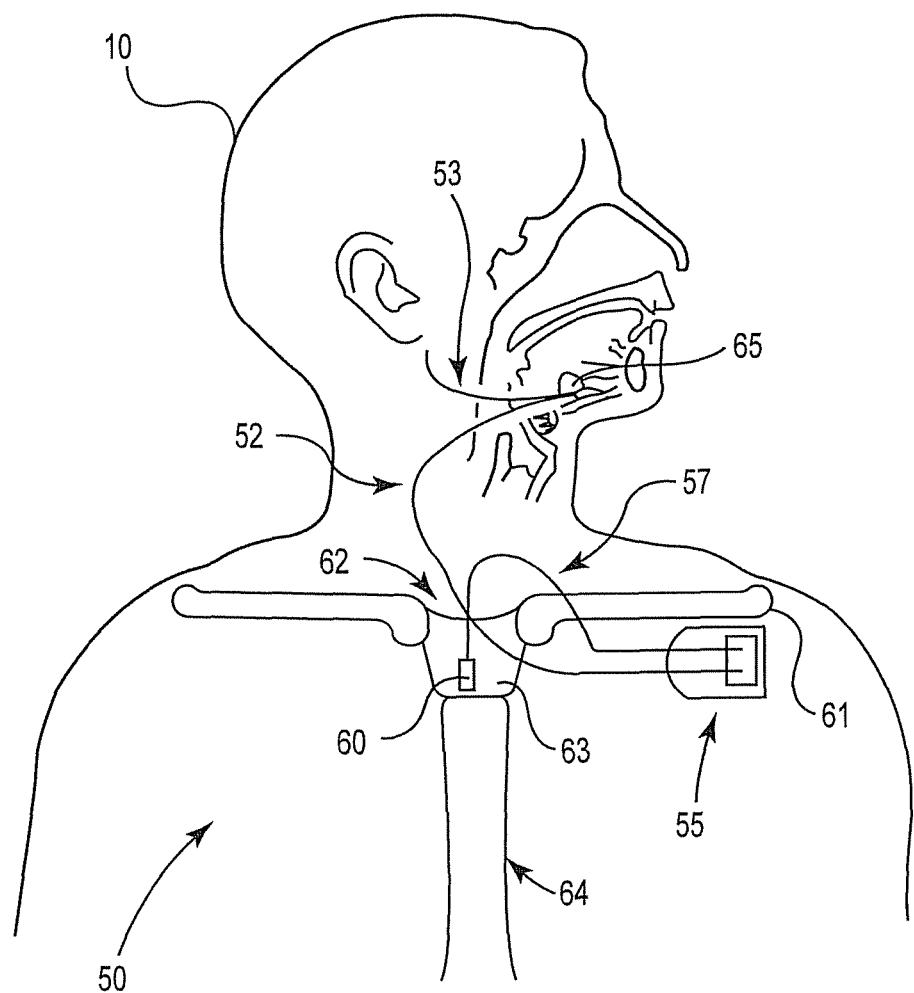
FIG. 1 is a schematic diagram of an implantable stimulation system that includes a self-expanding nerve cuff, according to an embodiment of the present disclosure.

FIG. 1 is a schematic diagram of an implantable stimulation system that includes a self-expanding nerve cuff, according to an embodiment of the present disclosure. As illustrated in FIG. 1, an example of an implantable stimulation system according to one embodiment of the present disclosure includes an implantable pulse generator (IPG) 55, capable of being surgically positioned within a pectoral region of a patient 10, and a stimulation lead 52 electrically coupled with the IPG 55 via a connector (not shown) positioned within a connection port of the IPG 55. The lead 52 includes an electrode or electrode system 65 and extends from the IPG 55 so that the electrode system 65 is position around a desired nerve, such as the hypoglossal nerve 53 of the patient 10, to enable stimulation of the nerve 53, as described below in detail. An exemplary implantable stimulation system in which lead 52 may be utilized, for example, is described in U.S. Pat. No. 6,572,543 to Christopherson et al., incorporated herein by reference in its entirety, and further includes a sensor lead 57 electrically coupled to the IPG 55 and extending from the IPG 55 so that a sensor or transducer 60 can be positioned in the patient 10 for sensing of respiratory effort.

The sensor 60 may be a pressure sensor that is surgically implanted in a region that has pressure continuity with the intrapleural space, such as the suprasternal notch, the space between the trachea and esophagus, or by being attached to either of the trachea or esophagus. The sensor 60 may also be positioned intercostally, or secured in a position for sensing pressure at the posterior side of the manubrium. The suprasternal notch 62 and manubrium 63 of the sternum 64 are well known structures on the upper chest that are in anatomical continuity with the intrapleural space. It is also well known that changes in intrapleural pressure provide a characteristic respiratory effort waveform.

The location for placement of the sensor 60 is, at least in part, chosen as a function of a delay, i.e. the propagation time associated with a pressure waveform characteristic of respiratory effort propagating from the respiratory point of origin to the sensor position. The chosen location is also a function of the amount of filtering necessary to achieve a usable sensed signal at a particular location, i.e. the amount of filtering that is necessary to remove waveforms other than the waveform associated with the desired sensed characteristic, such as the filtering required to remove cardiac waveform activity, for example. The positioning of the sensor 60 enables the IPG 55 to receive respiratory effort waveform information utilized to determine increased respiratory effort, which is then used by the IPG 55 to control delivery of therapy in response to determined increases in respiratory effort.

Figure 2:
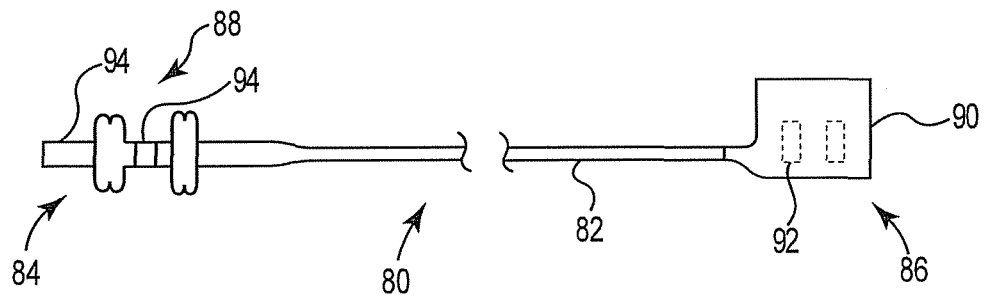
FIG. 2 is a side view of a lead utilized in an implantable stimulation system, according to an embodiment of the present disclosure.

FIG. 2 is a side view of a lead utilized in an implantable stimulation system according to an embodiment of the present disclosure. In one embodiment, as illustrated in FIG. 2, a lead 80 includes a lead body 82, connector 88, and an expandable cuff electrode 90. The lead body 82 extends from a proximal end 84 to a distal end 86, with the connector 88 being positioned at the proximal end 84 of the lead body 82 for electrically connecting the lead 80 to the IPG 55. The expandable electrode cuff 90 is located at the distal end 86 of the lead body 82 and is configured to be positioned around a target nerve, such as a hypoglossal nerve or other nerve. The electrode cuff 90 includes one or more electrodes 92 embedded within a wall of the electrode cuff 90 so that when the electrode cuff 90 is positioned around the nerve, the respective electrodes 92 are in contact with the nerve. In one aspect, the lead body 82 includes conductors (not shown) extending within the lead body 82 to electrically connect the electrodes 92 and the connector 88 so that the electrodes 92 are electrically coupled to the IPG 55 via respective connector pins 94 of the connector 88, as is known in the art.

Figure 3:
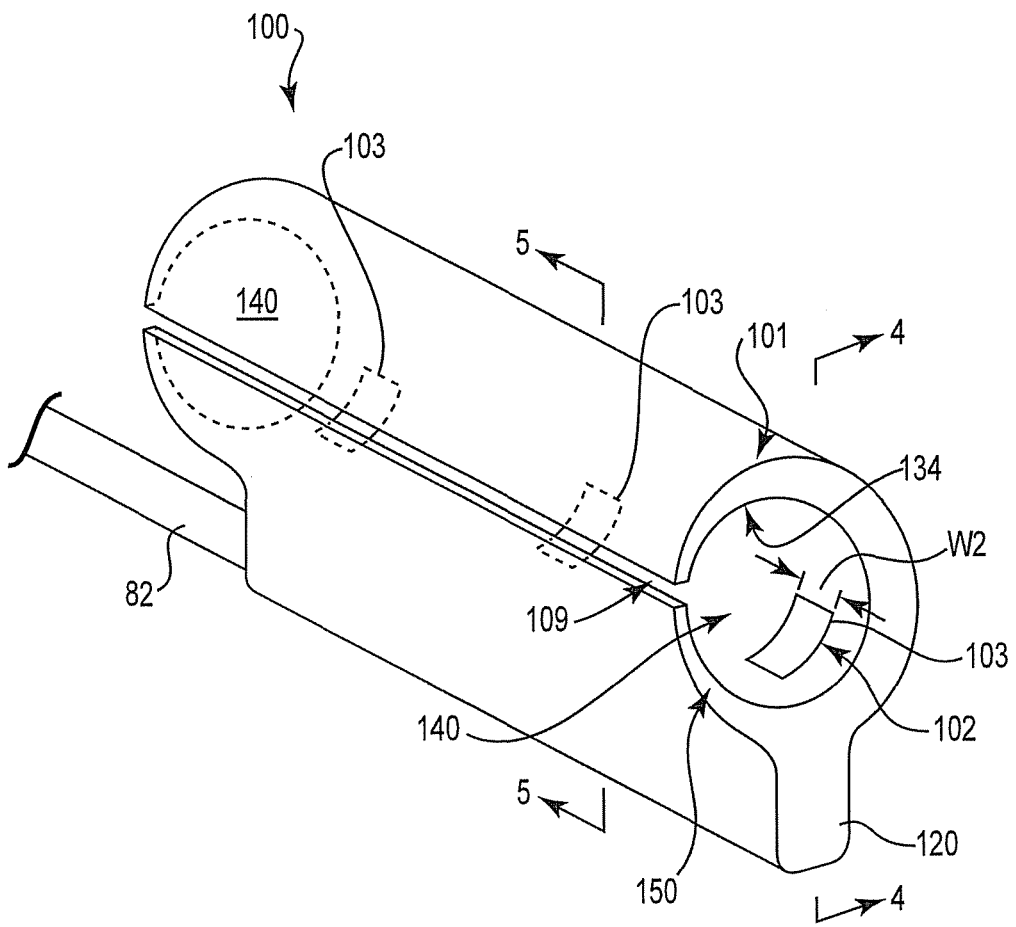
FIG. 3 is a perspective view of an expandable cuff electrode, according to an embodiment of the present disclosure.

FIG. 3 is a perspective view of an expandable electrode cuff 100, according to one embodiment of the present disclosure, which can be deployed in place of the cuff electrode 90 in lead 80. As illustrated in FIG. 3, cuff 100 includes a cuff body 101 and an array 102 of electrodes 103. In general terms, the cuff body 101 defines a lumen 140 through which a target nerve will extend. Among other features, the cuff body 101 includes a pair of resilient fingers 134, 150 (e.g., flange members) that have a generally arcuate shape and that extend from a base portion 120 of cuff body 101. In general terms, by pulling the ends of the resiliently, biased fingers 134, 150 apart from each other, access to lumen 140 is provided for engaging a target nerve. Upon release of the fingers 134, 150, the cuff body 101 resumes the shape illustrated in FIG. 3. As will be further described later, once positioned on a nerve, the materials and construction of the fingers 134, 150 permit automatic expansion of the size of lumen 140 to accommodate expansion of the size of the nerve encircled by the cuff body 101. In this manner, the electrodes 103 are held in close contact against the nerve while allowing for expansion of a diameter of lumen 140 defined between fingers 134, 150 and base 120.

In one embodiment, the array 102 of electrodes 103 are embedded within a wall of the cuff body 101 with the respective electrodes 103 spaced apart from each other along a length of the cuff body 101. In some embodiments, as illustrated in FIG. 3, the electrodes 103 are aligned in series along a single longitudinal axis on a common side or portion of the cuff body 101. However, in other embodiments, the electrodes 103 are staggered laterally relative to a single longitudinal axis or arranged in other patterns. In one embodiment, electrode 103 has a width (W2) of about 0.050 inches.

In some embodiments, cuff 100 additionally includes an outer flap or flange member that is biased and configured to maintain releasable coverage of at least a portion of an outer surface of the cuff body 101 and of the re-closable opening 109 between the distal ends of fingers 134, 150, as will be described in more detail in association with at least FIGS. 4-10. However, in other embodiments, this outer flap is omitted. In either case, FIG. 3 illustrates cuff body 101 without an outer flap for illustrative clarity in viewing the features and attributes of cuff body 101 that would otherwise be obscured by the presence of an outer flap.

Figure 4:
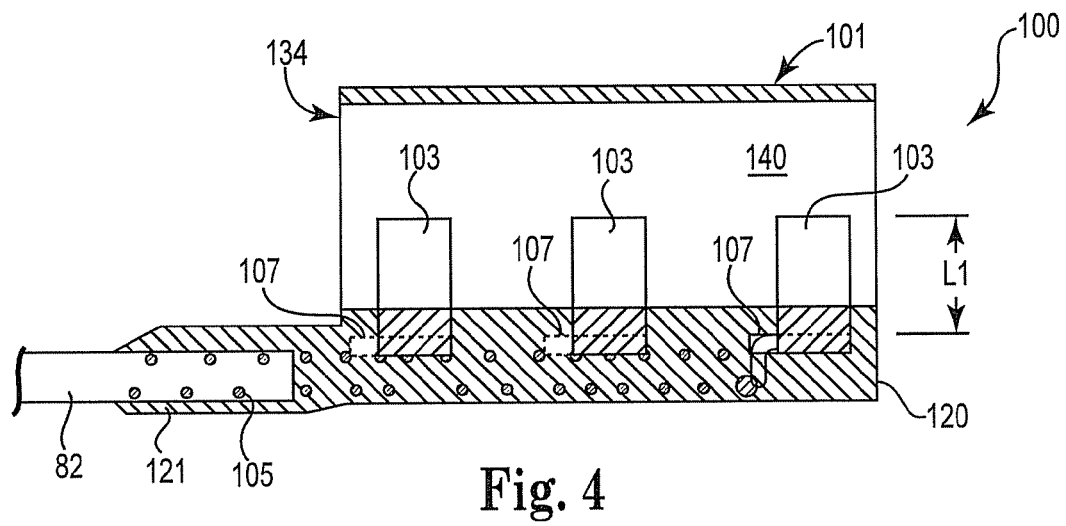
FIG. 4 is a sectional view as taken along lines 4-4 of FIG. 3, according to an embodiment of the present disclosure.

FIG. 4 is a sectional view of the expandable electrode cuff 100, as taken along lines 4-4 of FIG. 3, according to an embodiment of the present disclosure. As illustrated in FIG. 4, cuff 100 defines lumen 140 and provides a row of spaced apart electrodes 103 for contacting a nerve encircled by the cuff 100. Among other features, the cuff body 101 also includes a conductive coil 105 extending through a length of the body portion 120 and positioned to electrically connect to each of the respective electrodes 103. In some embodiments, it is understood that the coil 105 includes three separate coil components so that each electrode 103 is separately controllable via a respective one of the coil components to enable applying independent stimulation signals to the nerve from each electrode 103. In addition, in another aspect, base portion 120 includes a proximal extension 121 that extends proximally to mechanically connect the cuff body 101 to the lead body 82 while a proximal portion of the coil 105 is electrically connected to a conductive element of lead body 82. In one aspect, this proximal extension 121 serves as a strain relief to distribute forces from the lead body 82 to the electrode cuff 100 over a wider section of the lead body 82.

In one aspect, each electrode 103 includes a lower end to which a connector or crimp tube 107 (shown in FIG. 5) is mechanically and electrically attached, with a portion of the electrode coil 105 being mechanically and electrically connected to the crimp tube 107. In one non-limiting example, the crimp tube 107 and electrode 103 are metals suitable to be welded together to effect their mechanical and electrical connection together. In one aspect, the electrode is made from a biocompatible, non-corrosive electrically conductive material. In one non-limiting example, the electrode is made from a platinum-iridium material, such as a material including 90% platinum and 10% iridium. In another aspect, the coil 105 is made of a silver core MP35N type of conductor, although other types of non-silver conductors may be used. The silver component lowers the impedance of the lead, thereby providing a more efficient lead. Because of the specific attributes of these conductive materials, the material of the lead 82 is mechanically connected via crimping a portion of lead 82 to the crimp tube 107, thereby establishing the electrical connection between the coil 105 and the electrode 103.

Figure 5:
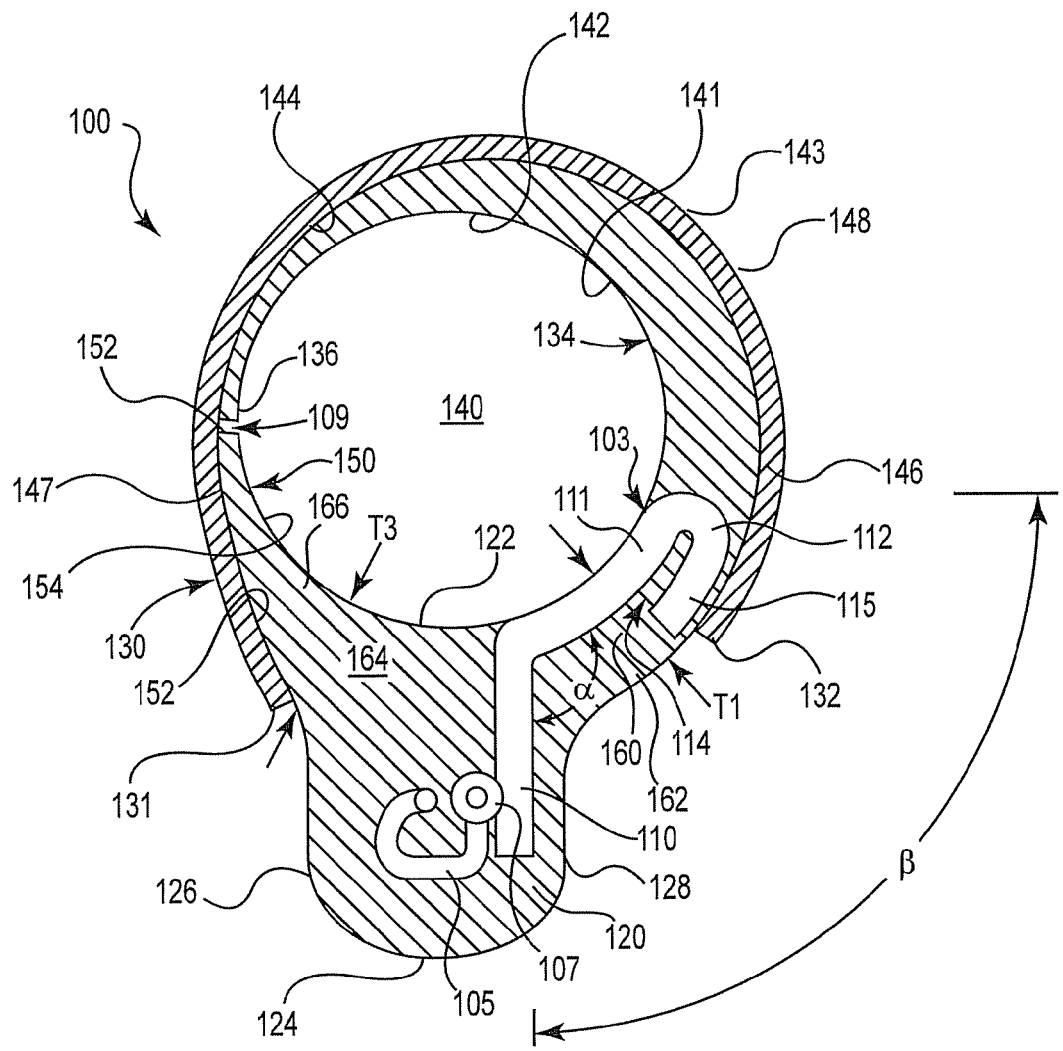
FIG. 5 is a sectional view as taken along lines 5-5 of FIG. 3, according to an embodiment of the present disclosure.

FIG. 5 is a sectional view of an expandable electrode cuff as taken along lines 5-5 of FIG. 3, according to an embodiment of the present disclosure. As illustrated in FIG. 5, in one embodiment an expandable electrode cuff 100 includes a base portion 120, a first flange member 130, a second flange member 134, and a third flange member 150. The base portion 102 includes a top wall 122, a bottom wall 124, a first side wall 126, and a second side wall 128. The second flange member 134 and the third flange member 150 comprise arcuate shaped fingers that are shaped, biased, and have a length to define a generally circular shaped lumen 140. The second flange member 134 extends generally outward from the second side wall 128 and from the top wall 122 of the base portion 120 with at least a portion of the second flange member 134 being spaced apart from the top wall 122 of the base portion 120. On the other hand, the third flange member 150 extends generally outward from the first side wall 126 and from the top wall 122 of the base portion 120.

In one aspect, the second flange member 134 has an arcuate length substantially greater than an arcuate length of the third flange member 150. In one embodiment, the second flange member 134 has an arcuate length substantially greater than (such as 3 times longer) an arcuate length of the third flange member 150. Moreover, in another aspect, the second flange member 134 includes a proximal portion 162 having a substantially greater width (such as 3 to 5 times greater) than a width of a distal portion 136 of the second flange member 134 and than a width of a distal portion 152 of the third flange member 150, as will be later described in more detail.

In some embodiments, the first flange member 130 includes a proximal end 131 and a distal end or portion 132 with the proximal end 131 being bonded to the third flange member 150 along a portion of an outer wall 152 of the third flange member 150. The first flange member 130 has a length sufficient to extend about, and be in releasable contact with, the periphery or outer surface of both the third flange member 150 and a majority of a length of the second flange member 134. In this arrangement, the first flange member 130 also extends over, and is spaced apart from, the top wall 122 of the base portion 120. In some embodiments, the first flange member 130 has an arcuate length equal to or greater than about one-half the circumference of an outer surface of the cuff 100 defined by the second and third flange members 134, 150. In this arrangement, with the first flange member 130 extending coextensively with (and in releasable contact with) a majority of the arcuate length of the second flange member 134, the first flange member 130 is biased to maintain coverage across the substantially re-closable opening 109 (between the distal ends 136, 152 of the respective second and third flange members 134, 150) even when a diameter of the lumen 140 increases.

In one aspect, the free distal portion (including distal end 132) of the first flange member 130 extends in a first direction or orientation opposite to the direction (or orientation) in which the free distal portion (including distal end 136) of the second flange member 134 extends. In this arrangement, with the first flange member 130 and the second flange member 134 being biased in an overlapping, releasably contacting relationship, each of the distal ends 132, 136 of the respective first and second flange members 130, 134 will move in opposite directions upon expansion of the lumen 140 in response to a swollen nerve or during positioning of the cuff 100 about a nerve, as will be further described in association with at least FIGS. 9-10.

In the expandable electrode cuff 100 of the embodiment of FIG. 5, the base portion 120, second flange member 134 and the third flange member 150 are formed from a single, unitary molded piece, with the first flange member 130 bonded to the molded piece. In other words, this single, unitary molded piece comprising the base member 120, second flange member 134, and third flange member 150 forms a monolithic component to which the first flange member 130 is attached. In some embodiments, first flange member 130 is attached via an adhesive (such as a polyurethane adhesive) or other bond.

FIG. 5 also illustrates one of the electrodes 103 that is embedded in cuff body 101, as previously illustrated in FIGS. 3-4. As illustrated in FIG. 5, electrode 103 includes a proximal base portion 110, a body portion 111, and a distal hook portion 112 with the distal hook portion 112 defining a recess 114 that extends between a distal tip portion 115 and body portion 111. In one aspect, each electrode 103 is a generally rigid member having electrically conductive properties, as will be later described in more detail. As illustrated in FIG. 5, the proximal base portion 110 is a generally straight portion while the body portion 111 extending distally from the base portion 110 includes a generally arcuate shape approximating the radius of curvature of the inner wall 142 of cuff body 101 that defines lumen 140. In one aspect, the body portion 111 forms a generally obtuse angle relative to the proximal base portion 110. In some embodiments, the obtuse angle (α) falls within a range of about 120 degrees to about 140 degrees. In one embodiment, the obtuse angle (α) is about 130 degrees.

In one embodiment, the arcuate length of the body portion 111 of electrode 103 generally corresponds to about a 45 degree arc (as represented by the arc β in FIG. 5) about the generally circular lumen 140. However, in some embodiments, the arcuate length of the body portion 111 of electrode 103 falls within a range that generally corresponds to about a 20 degree arc to about a 60 degree arc about the generally circular lumen 140 defined by cuff body 101.

In some embodiments, at least the body portion 111 of electrodes 103 has a thickness of about 0.006 inches. In some embodiments, the combination of the width W2 and the arcuate length (L1) of the body portion 111 defines a surface area available for contact against the target nerve. By limiting the arcuate length of the body portion 111 to a relatively short length that generally corresponds to about a 45 degree arc of the lumen 140, the generally rigid body portion 111 will be subject to little, if any, bending so that the body portion 111 and electrode 103 will be less likely to experience fracture or fatigue failures. However, given the relatively short length of body portion 111, the body portion 111 (and the rest of the electrode 103) is configured with a substantial width.

In one embodiment, the aspect ratio of the length to width of the electrode is about 1.2. However, in some embodiments, this aspect ratio can fall within a range from about to about 1 to 1.5. In this way, a generally optimal surface area of body portion 111 of electrode 103 is exposed to the nerve while maintaining a length of body portion 111 below a threshold at which a fatigue failure might be more likely to occur. In one aspect, the body portion 111 has a length that is long enough to engage a substantial portion (at least ¼ or a 45 degree arc) of a cross-section of the target nerve such that the exposed body portion 111 is limited to a length that minimizes the likelihood of fatigue through mechanical flexing while relatively maximizing the surface area of the exposed body portion 111 to maintain safe current densities.

In another aspect, during construction of the cuff 100, the cuff body 101 is molded in a manner to capture or embed the respective electrodes 103 within a portion of the cuff body 101. During this molding process, the material generally encapsulates the electrode 103, including filling in the recess 114 at the distal hook portion 112 of the electrode 103. In some embodiments, cuff body 101 is formed or molded as a single, monolithic member. However, in other embodiments, cuff body 101 is formed from two or more separate components. In either case, the cuff body 101 is molded or constructed to securely maintain electrode 103 within a fixed position relative to the remainder of the cuff body 102. In this regard, with the proximal base portion 110 of the electrode 103 extending within the base portion 120 and with the distal hook portion 112 extending within second flange member 134 at a location laterally spaced apart from the proximal base portion 110 of electrode 103, this arrangement ensures stability in the location of the electrode 103 relative to the cuff body 101. Moreover, as illustrated in FIG. 5, body portion 111 of electrode 103 is embedded within the thickest portion of the second flange member 134 so that cuff body 101 is substantially more rigid (i.e., less flexible) in the region of body portion 111 of electrode 103. Moreover, with this arrangement, body portion 111 becomes exposed at a lumen 140 to enable direct contact with a nerve extending through lumen 140.

In one aspect, because the electrode 103, and in particular the body portion 111, is made of a generally rigid material, the electrode 103 is substantially less likely to be subject to bending and/or fatigue failures during use within the body.

Moreover, because the electrode is generally rigid and is molded within the least flexible portion (e.g., the proximal portion 162 of second flange member 134) of the cuff body 101 as described above, the electrode 103 will not be subject to delamination (as typically occurs in foil-based electrode configurations of conventional electrode cuff arrangements) because the proximal portion 162 of the second flange member 134 that incorporates the body portion 111 and distal hook portion 112 of electrode 103 will not be subject to bending relative to the electrode 103, as will be later described in more detail in association with FIGS. 6-10, and FIG. 7 in particular. In one aspect, by full embedding the electrodes 103 (except for the exposed side of body portion 111), the cuff body 101 protects the nerve from the edges and corners of the electrode.

As described below in reference to FIGS. 5-10, the electrode cuff 100 is expandable both during implantation of the electrode cuff 100 (and associated lead 80), and is also automatically expandable (in response to a change in nerve diameter) after the electrode cuff 100 is positioned around a desired nerve for delivery of electrical stimulation therapy to the nerve, as was previously described in relation to FIGS. 3-5.

During its normal, unbiased state, prior to insertion around the nerve, the electrode cuff 100 is in a fully engaged position (shown in FIG. 5) in which, the second flange member 134 extends generally upward and outward from the second side wall 128 and over (i.e. above and spaced apart from) the top wall 122 of the base portion 120 with the distal end 136 terminating adjacent the distal end 152 of the third flange member 150. In this fully engaged position, the third flange member 150 extends generally upward and outward from the first side wall 126 and from the top wall 122 of the base portion 120 such that the third flange member 150 does not extend over the top wall 132. In one embodiment, the distal end 136 of the second flange member 134 is positioned adjacent to and in releasable contact against the distal end 152 of the third flange member 150 while in other embodiments, the respective distal ends 136 and 152 are in close proximity but do not contact each other. In general terms, these respective ends meet at a location along the first flange member 130 closer to the proximal end 131 than the distal end 132 of the first flange member 130. Together, the distal ends 136, 152 of the respective second and third flange members 134, 150 form a substantially re-closable opening 109 that provides selective access to lumen 140 and that generally maintains a nerve securely within the lumen 140, unless affirmative steps are taken to remove the electrode cuff 100 from the nerve.

In another aspect, while in this fully engaged position illustrated in FIG. 5, with the attachment of its proximal end 131 to the third flange member 150, the first flange member 130 extends generally outward from the first side wall 126 of the base portion 120 to be coextensive with and in releasable contact with an outer side wall 147 of the third flange member 150. It will be understood that the region of attachment of the first flange member 130 to the third flange member 134 extends over a significant portion of a length of the third flange member 150 to ensure a robust attachment. From this region, the first flange member 130 extends further over (e.g. above and spaced apart from) the top wall 122 of the base portion to be coextensive with, and in releasable contact with, an outer side wall 146 of the second flange member 134 until the distal end 132 terminates adjacent the top wall 122 of the base portion 120 on the second side 128 of the base portion.

In one aspect, the first flange member 130 has a length greater than a length of the second flange member 134 so that when the electrode cuff 100 is in the fully engaged position, the first, second and third flange members 130, 134 and 150 form a lumen 140 for receiving a nerve therein. With this in mind, an inner side wall 141 of the second flange member 134 and an inner side wall 154 of the third flange member 150 act together to form an inner wall 142 of the lumen 140 so as to position the electrodes 103 (shown in FIGS. 3-5), which are embedded within the second flange member 134, adjacent to the nerve (not shown in FIG. 3). In addition, when the electrode cuff 100 is in the fully engaged position shown in FIG. 5, an inner side wall 144 of the first flange member 130 is positioned in releasable contact against the outer side wall 146 of the second flange member 134 and against the outer side wall 147 of the third flange member 150. With this arrangement, an outer wall 148 of the first flange member 130 forms an outer wall 143 of the lumen 140. In this way, when the electrode cuff 100 is in the fully engaged position shown in FIG. 5, both the first flange member 130 and the second flange member 134 extend over (e.g., above and spaced apart from) the base portion 120 such that the first flange member 130 forms an outer layer of the electrode cuff 100, and such that the second and third flange members 134 and 150 form an inner layer of the electrode cuff 100 for engaging the nerve.

Depending on the size of the nerve about which the cuff 100 is mounted, the electrode cuff 100 may be either in the fully engaged position of FIG. 5 or in a partially fully engaged position (FIGS. 9-10), which occurs in the event that the cuff automatically expands in size to accommodate a larger sized diameter nerve or a swollen nerve. In a partially fully engaged position, the general configuration of the electrode cuff 100 remains generally the same as the fully engaged position except that, because the first flange member 130 is slidably movable relative to the second flange member 134 and because the generally flexible, distal portion of the second flange member 134 permits rotational movement of the second flange member 134 away from the third flange member 150, the distal end 132 of the first flange member 130 will be positioned along the outer side wall 146 of the second flange member 134 in a location spaced further away from the second side wall 128 than shown in FIG. 5. Likewise, upon rotation of the second flange member 134 away from the third flange member 150, the substantially re-closable opening between the distal end 136 of the second flange member 134 and the distal end 152 of the third flange member 150 will at least partially open as a gap between the distal ends 136, 152, as will be further described below. Nevertheless, despite this gap, in the partially fully engaged position the lumen 140 remains generally closed because the first flange member 130 has a length sufficient to still extend across the gap (in the substantially re-closable opening) between the respective distal ends 136, 152 and to extend further over (and in releasable contact with) substantial remaining portions of the second flange member 134.

In some embodiments, the respective flange members 130, 134, 150 are configured with a relative thickness, shape, and sufficient flexibility (in the resilient materials forming them) such that a force that would cause the cuff electrode 109 to expand to a larger diameter size is less than the capillary blood flow pressures in the vessels along the nerve. In one aspect, this arrangement ensures that the cuff electrode 100 will not restrict blood flow to the nerve.

Figure 6:
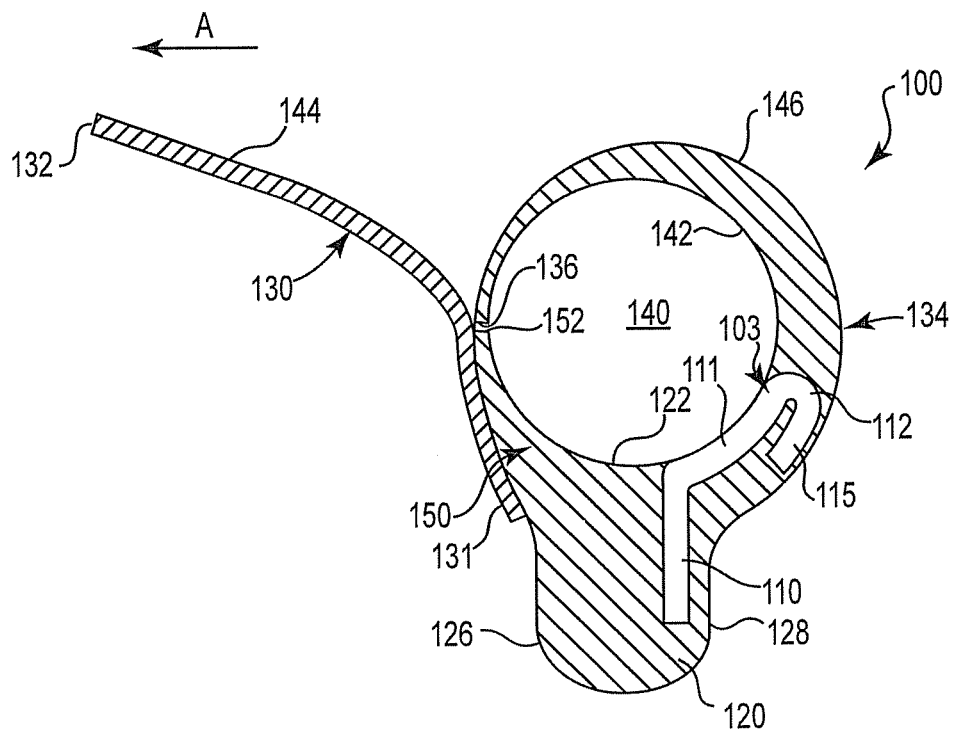
FIG. 6 is a sectional view of the expandable cuff of FIG. 5 in an intermediate open position, according to an embodiment of the present disclosure.

FIG. 6 is a sectional view of the expandable cuff of FIG. 5 in an intermediate open position, according to an embodiment of the present disclosure. As illustrated in FIG. 6, during positioning of the electrode cuff 100 over the desired nerve so that the nerve can be properly located within the lumen 140, the electrode cuff 100 is advanced from the fully engaged position shown in FIG. 5, to an intermediate open position shown in FIG. 6. In this intermediate position, beginning with distal end 132, the first flange member 130 is pulled in a first direction (represented by arrow A) away from the second side wall 128 of base portion 120 and away from the second flange member 134 to cause the distal end 132 of the first flange member 130 to extend generally outward in an opposite direction from the first side wall 126 of the base portion 120. As a result, when the electrode cuff 100 is in the intermediate open position, the first flange member 130 is positioned so as to not extend over (e.g. above and spaced apart from) the top wall 122 of the base portion 320. However, in this position, the lumen 140 remains generally closed because the second flange member 134 remains positioned to extend over the top wall 122 of the base portion 120, with the distal end 136 of the second flange member 134 terminating adjacent to the distal end 152 of the third flange member 150. Finally, when the cuff 100 is in the intermediate open position of FIG. 6, the inner side wall 144 of the first flange member 130 is no longer positioned over and adjacent to the outer side wall 146 of the second flange member 134.

Figure 7:
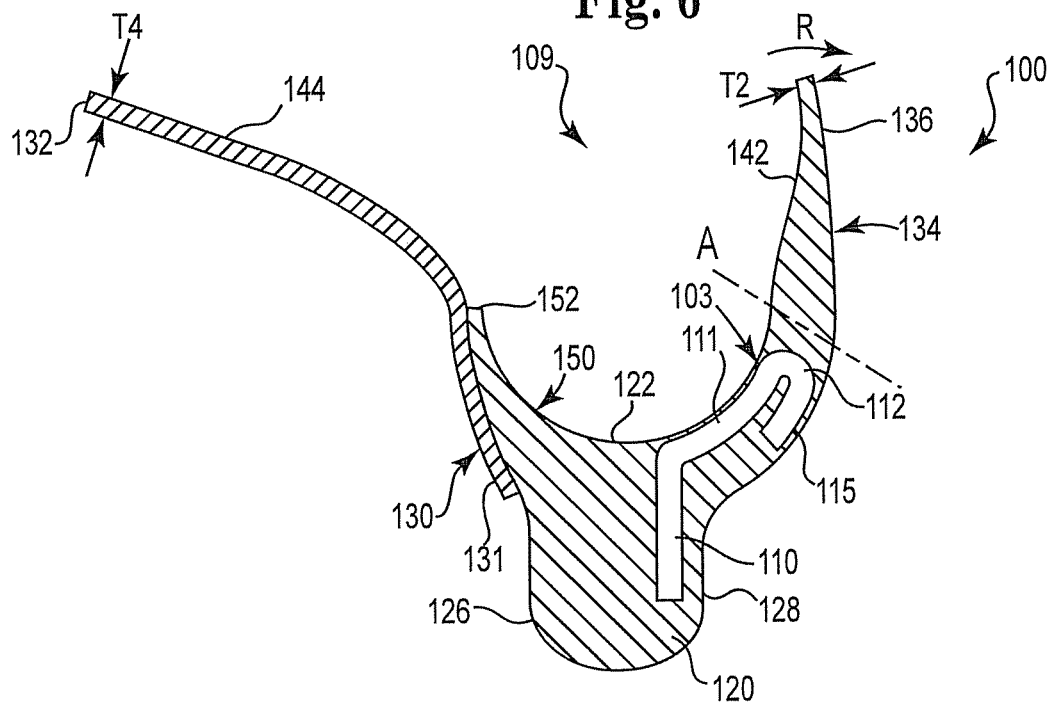
FIG. 7 is a sectional view of the expandable electrode cuff of FIG. 5 in a fully open position, according to an embodiment of the present disclosure.

FIG. 7 is a sectional view of the expandable electrode cuff of FIG. 5 in a fully open position, according to an embodiment of the present disclosure. As illustrated in FIG. 7, once the electrode cuff 100 is in the intermediate open position, the distal end 136 of the second flange member 134 is moved away from the distal end 152 of the third flange member 150 in a second direction (opposite the first direction A in FIG. 6). With this maneuver, a majority of the second flange member 134 is rotated away from third flange member 150 (as represented by directional arrow R) to no longer extend over or above the top wall 122 or above the first side wall of the base portion 120. In this arrangement, the distal end 136 of the second flange member 134 extends outward in the opposite direction from the second side wall 128 of the base portion 120, resulting in the inner wall 142 of the second flange member 134 no longer forming the lumen 140 when the electrode cuff 100 is in the fully open position of FIG. 7. In addition, in this position, the large gap in the re-closable opening 109 defined between the distal ends 136, 152 of the respective second and third flange members 134, 150 facilitate installation of the cuff 100 about a nerve. Accordingly, when the electrode cuff 100 is in the fully open position, this configuration includes: (1) neither the first flange member 130 nor the second flange member 134 being positioned to extend over the top wall 122 of the base portion 120 of the electrode cuff 100; (2) the inner side wall 144 of the first flange member 130 no longer overlapping (or near) the outer side wall 146 of the second flange member 134; and (3) the inner side wall 141 of the second flange member 134 no longer defining the inner wall 142 of the lumen 140 (because the lumen 140 is temporarily deconstructed).

In this way, by enabling the electrode cuff 100 to be advanced between the fully engaged position (FIG. 5), the intermediate open position (FIG. 6), and the fully open position (FIG. 7), the electrode cuff 100 can be more easily positioned over a nerve during implantation of the lead 80.

As can be seen in FIGS. 5-7, the second flange member 134 according to one embodiment has a first thickness (T1 at 160) along a proximal end 162 of second flange member 134 located adjacent the top wall 122 of the base portion 120 along the second side wall 128, and has a second thickness (T2 in FIG. 7), less than the first thickness (T1 at 160), at the distal end 136 of the second flange member 134. In this arrangement, the second flange member 134 is tapered in thickness from the proximal end 162 to the distal end 136. Similarly, the third flange member 150 has a first thickness (T3 at 164 in FIG. 5) along a proximal end 166 located near the top wall 122 of the base portion 120 along the first side wall 126, and a second thickness (T4 in FIG. 7), less than the first thickness 164, at the distal end 152 of the third flange member 150. In this arrangement, the third flange member 150 is tapered in thickness from the proximal end 166 to the distal end 152. While the inner flange member 134 of FIGS. 5-7 is shown to be tapered, it is understood that the inner flange member 134, inner flange member 150, and/or the outer flange member 130 could be formed without being tapered. As described above, with the proximal portion 162 of the second flange member 134 being substantially less flexible than the distal end 136, the second flange member 134 is biased to maintain the curved shape defining lumen 140 while still permitting selective opening of the re-closable opening 109 via maneuvering the distal end 136 relative to the third flange member 150.

In one embodiment, the flange members 130, 134, 150 described above are formed from polyurethane, silicon or a blend of polyurethane and silicon. Furthermore, according to some embodiments, one of the flange members could be formed of polyurethane while the other is formed of silicon. If formed from silicone, then the durometer of the flange material range would be within a range of approximately 40 A-70 A. In some embodiments, the thickness of the flange material would be from approximately 0.005 inches to 0.025 inches. Nominally, if the flange is formed of a polyurethane material having a durometer of approximately 85 A, the flange would be 0.0075 inches thick. In the embodiment of FIGS. 5-7, the inner flanges 134, 150 are formed from molded polyurethane and the outer flange 130 is formed from a portion of a polyurethane tubing. In either embodiment, the polyurethane is formed to have a "memory" that enables the flange members to be biased towards the fully engaged positioned. In some embodiments, the lumen 140 will have an inner diameter between 0.050 and 0.400 inches, while according to one embodiment, the inner diameter is approximately 0.140 inches in the fully engaged position.

If the inner flange members 134, 150 are tapered, their respective proximal portion 162, 166 have a thickness of approximately 0.025 to 0.030 inches, and their respective distal ends 136, 152 have a thickness of approximately 0.001 to 0.010 inches. In addition to the features described above, in one embodiment, by providing a relatively thicker base or proximal end, this arrangement provides a strong mechanical connection relative to the base portion 120 and also provides the needed thickness to hold, and provide strain relief, for the electrodes 103. According to one embodiment, the distal end 136 of second flange member 134 has a thickness of about 0.005 inches. Similarly, in one embodiment, the distal end 152 of the third flange member 150 has a thickness of about 0.005 inches.

Figure 8:
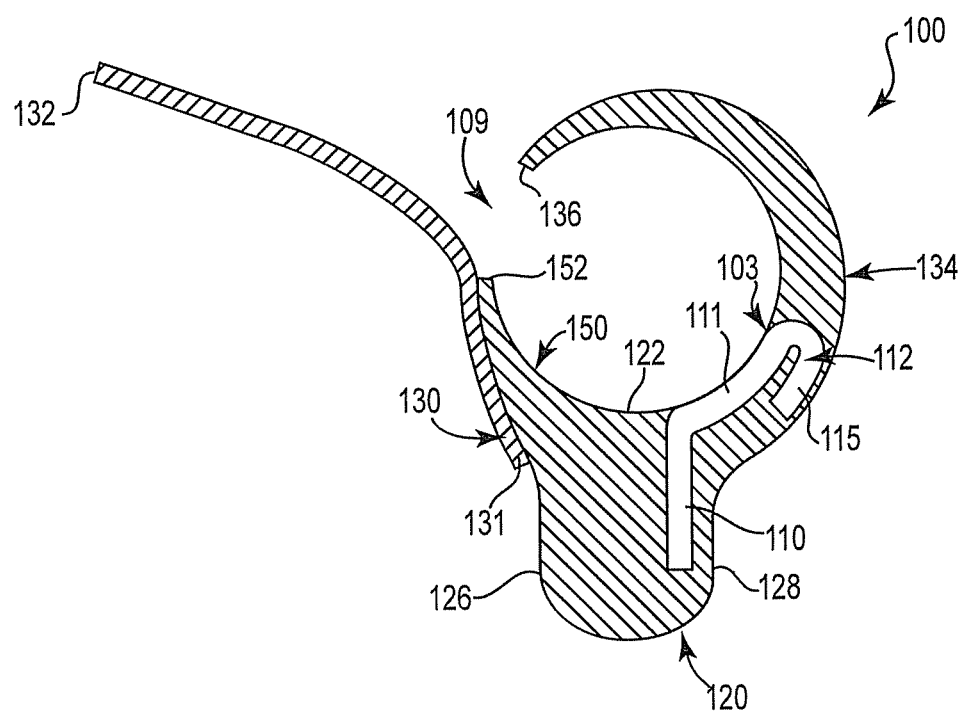
FIG. 8 is a sectional view of an expandable electrode cuff in an intermediate open position, according to an embodiment of the present disclosure.

FIG. 8 is a sectional view of the expandable electrode cuff of FIG. 5 in an intermediate open position, according to an embodiment of the present disclosure. As illustrated in FIG. 8, depending upon the circumference of the nerve, the nerve will become positioned over the top wall 122 of the base portion 120 of the electrode cuff 110, adjacent to the third flange member 150, and against body portion 111 of electrode 103 at the proximal portion 162 of second flange member 134. Accordingly, once the second flange member 134 is positioned about the nerve during the advancement of the electrode cuff 100 from the fully open position of FIG. 7 to the intermediate open position, then the distal end 136 of the second flange member 134 will be positioned to be spaced further above the proximal end 131 of the first flange member 130 and the distal end 152 of the third flange member 150 (than when the electrode cuff 100 is in the intermediate open position of FIG. 6). This arrangement results in a substantial gap forming in the re-closable opening 109. In this way, the size of the lumen 140 can be increased relative to when the electrode cuff 100 is in the intermediate open position of FIG. 6 to accommodate the size of the nerve during positioning of the electrode cuff 100.

Figure 9:
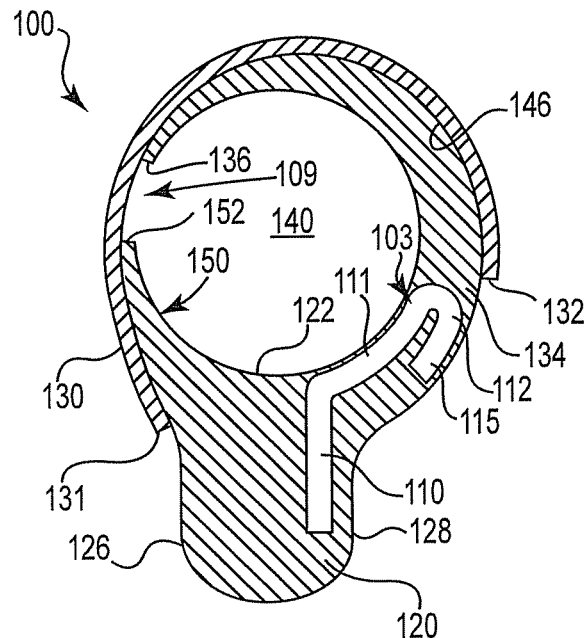
FIG. 9 is a sectional view of an expandable electrode cuff in a larger diameter, fully engaged position, according to an embodiment of the present disclosure.

FIG. 9 is a sectional view of the expandable electrode cuff of FIG. 5 in a fully engaged position, according to an embodiment of the present disclosure, when cuff 100 is deployed on a larger diameter nerve as noted in association with FIG. 8. Similarly, during the advancement of the electrode cuff 100 from the intermediate open position of FIG. 8 to the fully engaged position during implant of the electrode cuff 100, first flange member 130 is allowed to return, via the biasing action, to its at-rest configuration to extend coextensively with (and in releasable contact with) the second flange member 134 and also cover the re-closable opening 109. Moreover, the distal end 132 of the outer flange member 130 may be positioned along the outer side wall 146 of the second flange member 134 to be spaced further away from the second side wall 128 than when the electrode cuff 100 is in the fully engaged position of FIG. 5, and to be above, rather than below the top wall 132 of the base portion 120 (as in FIG. 3). As a result, the diameter of the lumen 140 is increased relative to when the electrode cuff 100 is in the fully engaged position of FIG. 5 prior to being implanted, to accommodate the size of the nerve. Therefore, as illustrated in at least FIGS. 8-9, in order to accommodate the size of the nerve, the first flange member 130 and second flange member 134 are movable in oppositely-oriented directions to allow an increase in the diameter of the lumen 140.

Figure 10:
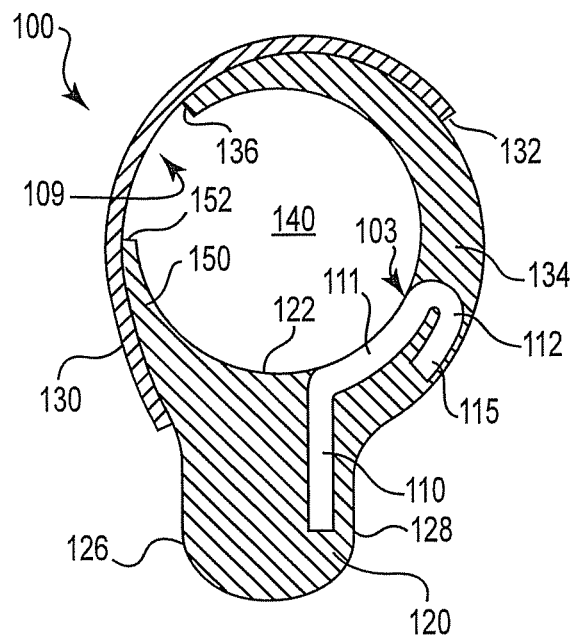
FIG. 10 is a sectional view of an expandable electrode cuff in another larger diameter, fully engaged position, according to an embodiment of the present disclosure.

FIG. 10 is a sectional view of the expandable electrode cuff of FIG. 5, according to an embodiment of the present disclosure. As illustrated in FIG. 10, according to one embodiment, in order to address the effects of swelling of the hypoglossal nerve that may sometimes occur, particularly after the initial trauma associated with implanting the electrode cuff 100, the first and second flange members 130 and 134 are expandable so that the circumference of the lumen 140 formed by the electrode cuff 100 can be increased to accommodate increases in the diameter of the nerve that occur subsequent to the initial positioning of the expandable electrode cuff 100 about the nerve, as illustrated in FIG. 9. For example, during swelling of the nerve subsequent deploying the electrode cuff 100 about the nerve and implanting the rest of the lead 80, the first flange member 130 and the second flange member 134 slidably move in opposite directions relative to each other as lumen 140 expands to accommodate the increased diameter of the nerve. During this expansion, the distal end 132 of the first flange member 130 becomes positioned to be spaced further away from the second side wall 128 of the base portion 120, and to be even further above, rather than below, the top wall 122 of the base portion 120 than when the electrode cuff 100 was initially positioned about the nerve to the position illustrated in FIG. 9. At the same time, during this expansion of lumen 140, the second flange member 134 rotates away from the third flange member 150 such that the distal end 136 of the second flange member 134 becomes positioned to be spaced further above the distal end 152 of the third flange member 150, and to be further away from the first side wall 126 and the top wall 122 of the base portion 120, thereby further increasing the size of the lumen 140 to accommodate the swelling. As a result, there is a further increase in the size of the gap of re-closable opening 109. Nevertheless, as illustrated in FIG. 10, with first flange member 130 still covering (i.e., extending across) this re-closable opening 109, closure of lumen 140 about the nerve is maintained so that contact is maintained between the body portion 111 of electrodes 103 and the nerve, yet without placing undue pressure on the nerve. As the swelling of the nerve subsides some period of time after implanting the lead 80 and cuff 100, the first and second flange members 130 and 134 return towards the original fully engaged position about the nerve that occurred during positioning of the electrode cuff 100 at the time of implant of the lead 80 and electrode cuff 100, such as is illustrated in FIG. 9.

By forming the first and second flange members 130, 134, described above, to extend over the base member 120 so that each of the flange members 130, 134 extend from a proximal end (e.g., 131 and 162, respectively) located on one side of the base member to a distal end (e.g., 132 and 136, respectively) located along the other side of the base member, the electrode cuff will continue to be positioned completely around the nerve. This overlapping, slidably movable relationship between the first flange member 130 and the second flange member 134 and the overlapping relationship between the first flange member 130 and the third flange member 150 prevents open gaps from being formed between the distal ends 136, 152 of the respective flange members 130, 134, 150 as the nerve swells. Rather, the first and second flange members 130, 134 described above enable the expansion of the flange members, as warranted, to accommodate increasing the diameter of the lumen 140 in order to maintain enclosure of the nerve within the lumen. In this way, using the electrode cuff 100 described above, the opportunity for a portion of the nerve to become displaced external to the lumen 140 is minimized because the electrode cuff 100 is able to more effectively accommodate such swelling of the nerve.

In general terms, the interrelationship between a combination of the first flange member 130, second flange member 134, and third flange member 150 provides an electrode cuff that remains securely engaged about a nerve but that also automatically adjusts its diameter to accommodate a swollen nerve or nerves that have a larger diameter. In one aspect, this combination of the respective interacting flange members 130, 134, 150 achieves the secure fixation and automatic adjustability of the electrode cuff 100 without using a clamp, buckle, hinge/pin found in conventional electrode cuffs. Rather, the spatial arrangement and selective overlapping relationship between the respective flange members, as well as the resilient (e.g., configured to generally maintain or return to a pre-formed shape) material forming those flange members and the tapered configuration of the respective flange members 134, 150, enables the electrode cuff 100 to provide the secure fixation and/or automatic sizing adjustment (i.e., both the expandability and the contraction to a minimum diameter) that maintains efficacious nerve contact while minimizing undue pressure on the nerve.

Figure 11:
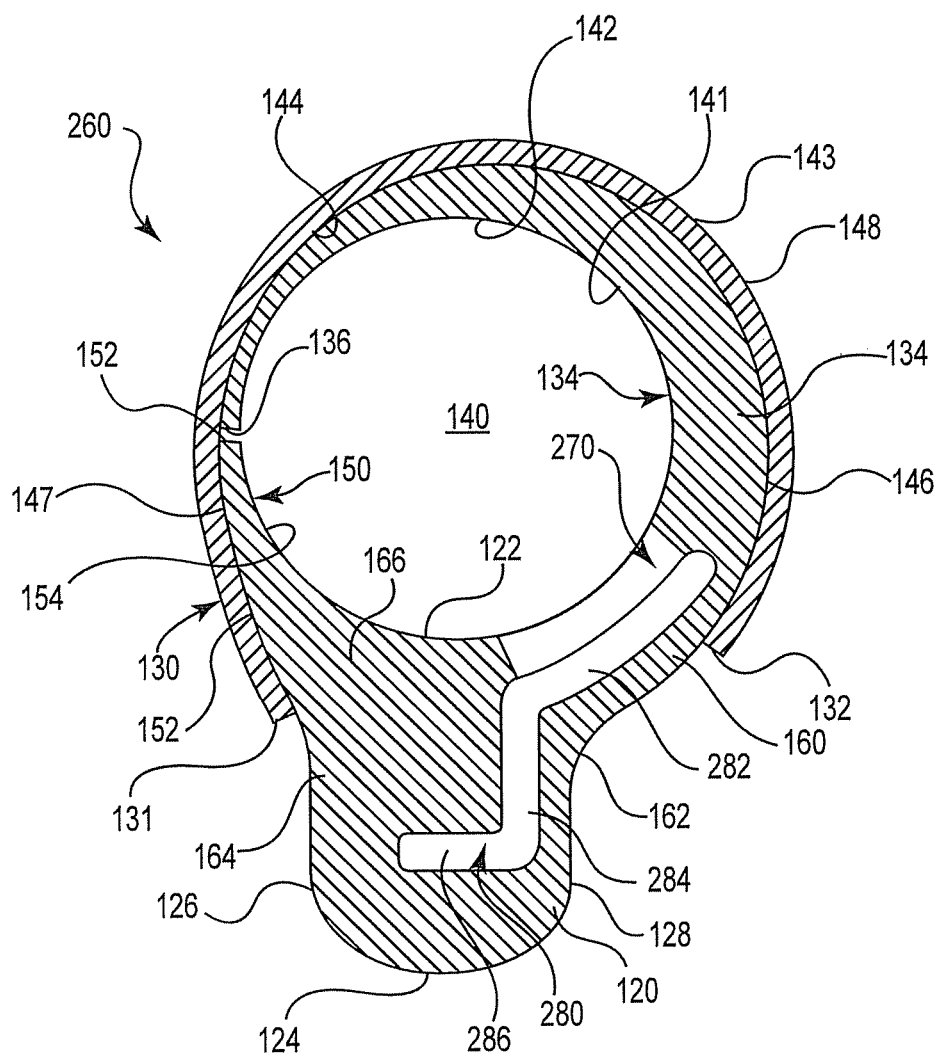
FIG. 11 is a sectional view of an expandable electrode cuff in a fully engaged position, according to an embodiment of the present disclosure.

FIG. 11 is a sectional view of an expandable electrode cuff 260, according to an embodiment of the present disclosure. In one embodiment, this expandable electrode cuff 260 comprises substantially the same features and attributes as the electrode cuff 100 that was previously described in association with FIGS. 5-10, except for the presence of a recess 270 in an inner wall portion 142 of the lumen 140 and the recessed position of a body portion 282 (like body portion 111 in FIG. 5) of an electrode 280 embedded within the cuff body 101. In addition, in some embodiments, instead of having a distal hook portion 112 as in the cuff 100 of FIGS. 5-10, electrode 280 omits a distal hook portion. However, at its proximal end, the electrode 280 does not terminate with the proximal base portion 284 (like proximal base portion 110 in FIG. 5). Instead, as illustrated in FIG. 11, the electrode 280 additionally includes a lateral portion 286 that extends laterally and generally perpendicular to the proximal base portion 280 in a direction generally opposite from the direction in which the body portion 282 extends laterally outwardly from the proximal base portion 280.

In one aspect, the configuration of the body portion 282 and the lateral portion 286 being at opposite ends of the base portion 284, and extending outwardly in opposite directions relative to the base portion 284, provides a multi-directional shape that anchors electrode 280 securely relative to the base portion 120 and second flange member 134 of cuff 100 upon molding the cuff 100 about the electrode 280.

It is also understood that in some embodiments, the configuration of the electrode 280 in the embodiment of FIG. 11 can be substituted for the electrode 103 in the embodiments of FIGS. 5-10, whether the recess 270 is present or absent.

Figure 12:
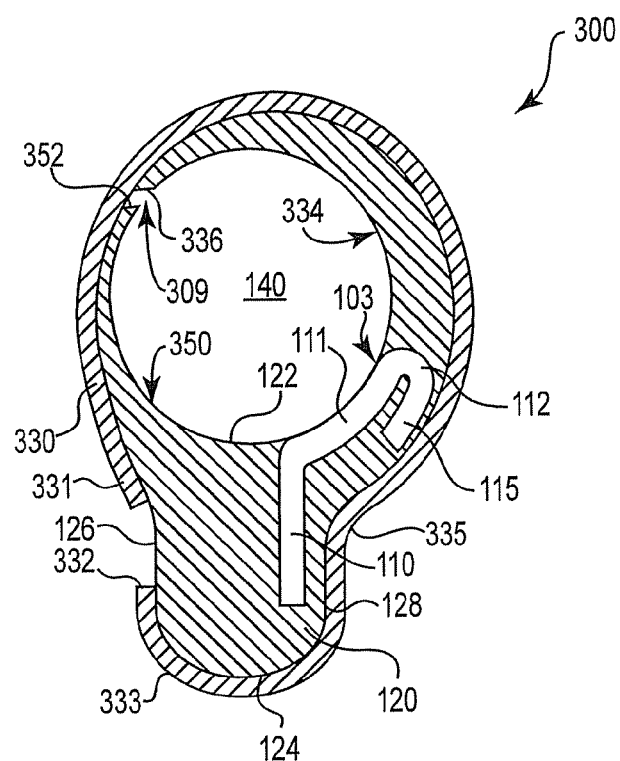
FIG. 12 is a sectional view of an expandable electrode cuff in a fully engaged position, according to an embodiment of the present disclosure.
Figure 13:
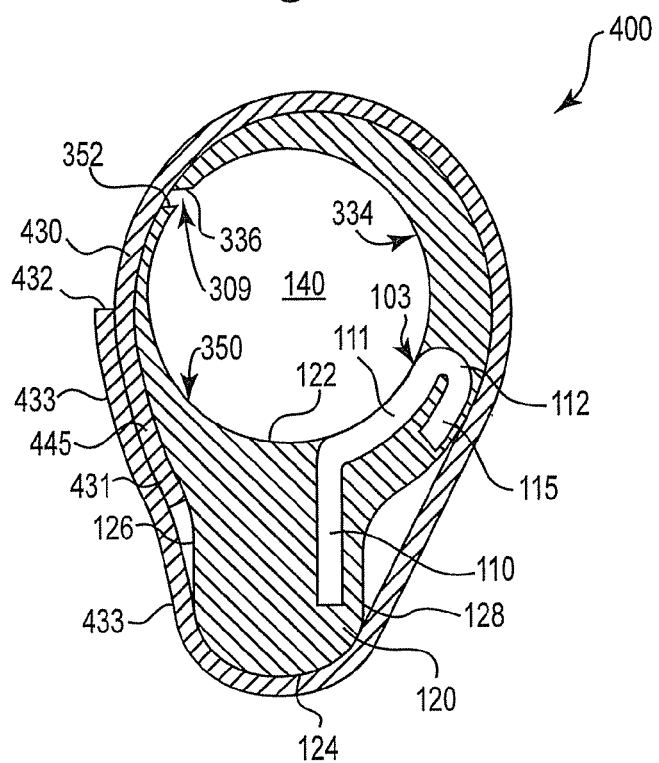
FIG. 13 is a sectional view of an expandable electrode cuff in a fully engaged position, according to an embodiment of the present disclosure.

FIGS. 12-13 are sectional views of expandable electrode cuffs 300, 400, according to some embodiments of the present disclosure. In one embodiment, the respective electrode cuffs 300, 400 include at least substantially the same features and attributes of the electrode cuff 100 as previously described in association with FIGS. 5-10, except for modifying the relative lengths of the second flange member and the third flange member and for modifying a length and position of a first flange member relative to the base portion of the electrode cuff 300.

As illustrated in FIG. 12, electrode cuff 300 includes a second flange member 334 that is generally shorter (than the second flange member 134 of FIG. 5) and a third flange member 350 that is generally longer (than the third flange member 150 in FIG. 5) such that a point of releasable contact (such as the re-closable opening 139) between the respective distal ends 336, 352 of these flange members is generally spaced farther above the top wall 122 of base portion 120. In one non-limiting aspect, by providing a different point (in comparison to the cuff 100 of FIG. 5) of re-closable opening 309 for the second flange member 334 and the third flange member 350 to provide access to lumen 140, electrode cuff 300 provides a configuration that may be more suitable to deployment in different anatomical environments than electrode cuff 100 and/or that is more suitable to modified deployment techniques to engage a target nerve. It will be understood that at the time of construction one can select the relative lengths of the second and third flange members 334, 350 to effectively select the point of releasable contact via re-closable opening 309 between the distal ends 336, 352 of the second and third flange members 334, 350 at many desired location within along the circumference of the lumen 140.

In addition, in some embodiments, the length of the first flange member 330 is increased (in comparison to a length of first flange member 130 in FIG. 5) so that the distal end 332 of the first flange member 430 terminates along the first side wall 126 instead of terminating along a proximal end 162 of second flange member 134 as in embodiment of FIG. 5. Accordingly, in this arrangement, extending from its proximal end 331, the first flange member 334 extends alongside the third flange member 350, around the entire second flange member 334, along the second side wall 128 and bottom wall 124 of the base portion 120 before terminating along the first side wall 126 of base portion 120. In this releasably secured position, the distal end 332 of first flange member 330 is located below, and spaced apart from, the proximal end 331 of the first flange member 330.

As illustrated in FIG. 12, in some embodiments, the first flange member 330 is pre-formed to include a transition region 335 configured to substantially match the contour of the transition between the second flange member 334 and the second side wall 128 of the base portion 120. This arrangement facilitates maintaining releasably secure contact of the first flange member 330 against the second flange member 334 and base portion 120. Moreover, in some embodiments, the first flange member 330 also is pre-formed to include a distal cap region 333 configured to substantially match the generally arcuate contour of the bottom wall 124 of the base portion 120 (as it extends between first side wall 126 and the second side wall 128). This arrangement facilitates maintaining releasably secure contact of the first flange member 330 against the base portion 120. Accordingly, the extra length and pre-formed shape of the first flange member 330 provides a more secure arrangement in which the distal end 331 of first flange member 330 cannot be automatically, slidable movable relative to the second flange member 334.

However, it is understood that the extra length of the first flange member 330 can be provided as shown in FIG. 12 without requiring that the transition region 335 and the distal cap region 333 be pre-formed to match the contour of the reciprocating shape portions of the base portion 120 or the second flange member 334.

FIG. 13 is a sectional view of an electrode cuff 400, according to an embodiment of the present disclosure. In one embodiment, electrode cuff 400 includes substantially the same features and attributes as the embodiment of FIG. 12, except for the differences noted below in association with FIG. 13. As illustrated in FIG. 13, according to another embodiment, the length of a first flange member 430 is increased even further so that instead of the distal end 332 of the first flange member 330 (as in FIG. 12) terminating along first side wall 126, the distal end 432 of the longer first flange member 430 terminates alongside a portion of the third flange member 450 and the first flange member 430. In this arrangement, a distal portion 433 of first flange member 430 overlaps a proximal portion 445 of the first flange member 430 so that the distal end 432 of the first flange member 430 is positioned above the proximal end 431 of the first flange member 430. In another aspect, as illustrated in FIG. 13, the first flange member 430 does not include one or more pre-formed regions that substantially match the contour of the base portion 120, as was previously described in association with some embodiments of the electrode cuff 300 of FIG. 12. Nevertheless, the relatively longer distal portions of the first flange member 430 that extend beyond the first side wall 126 of base portion still exert and provide a more secure fixation of the electrode cuff 400 so that electrode cuff 400 provides greater resistance to and/or generally prevents automatic expansion of lumen 140, as can occur more readily with the embodiment of FIG. 5 in which the first flange member 130 has a generally shorter length (and which thereby provides less frictional resistance).

Figure 14:
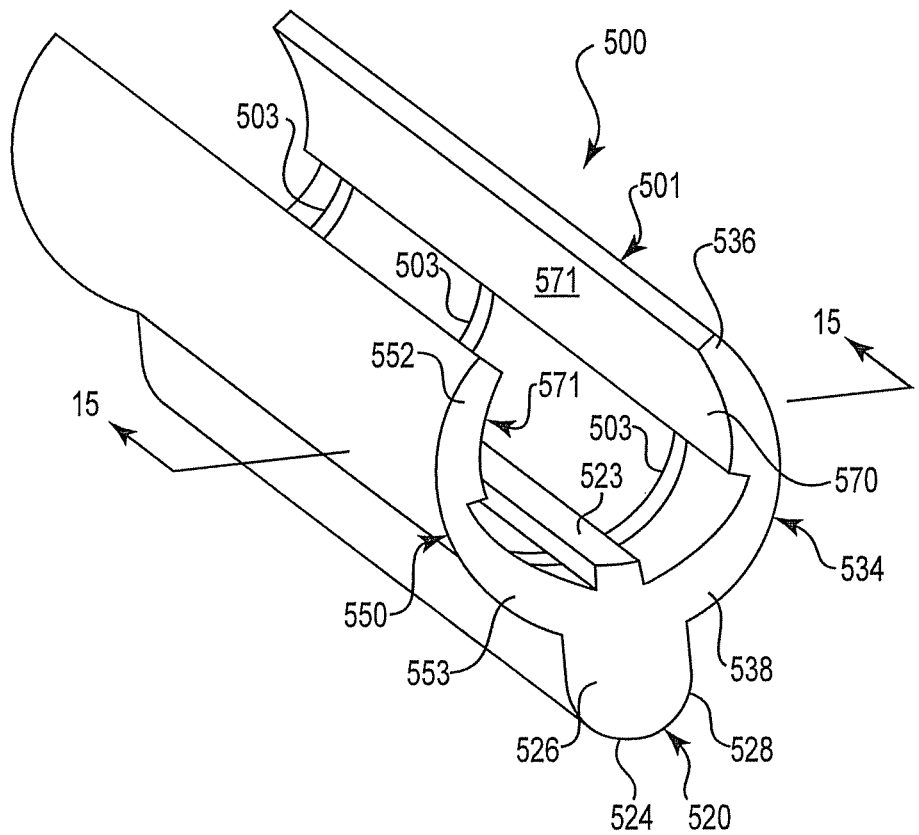
FIG. 14 is a perspective view of an expandable electrode cuff, according to an embodiment of the present disclosure.

FIG. 14 is a perspective view of an electrode cuff 500, according to an embodiment of the present disclosure. In one embodiment, while the electrode cuff 500 includes a differently configured electrodes 503 and differently configured flange members 534, 550, it will be understood that the electrode cuff 500 includes substantially the same choice of materials for the electrodes and flange members, and is molded in generally the same manner, as previously described in association with FIGS. 5-13 (unless noted otherwise).

Figure 15:
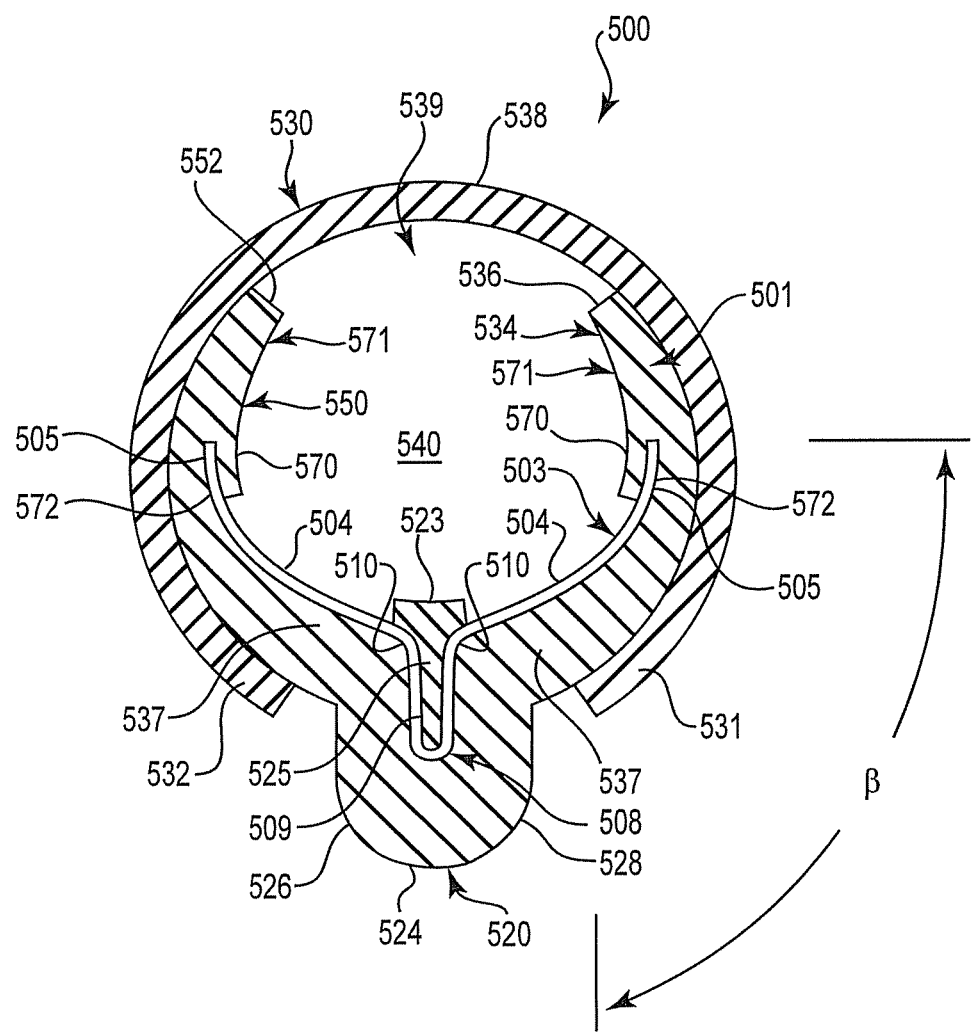
FIG. 15 is a sectional view as taken along lines 15-15 of FIG. 14, according to an embodiment of the present disclosure.

As illustrated in FIG. 14, electrode cuff 500 comprises an elongate cuff body 501 that includes at least a base portion 520, second flange member 534 and the third flange member 550. It will be understood that while electrode cuff 500 generally includes a first flange member 530 as shown in FIG. 15, FIG. 14 omits this first flange member 530 for illustrative clarity to better depict the second and third flange members 534, 550. The base portion 520 includes a bottom wall 524, first side wall 526, and second side wall 528, and top wall 522.

However, in some embodiments, the top wall 522 includes a ridge or protrusion 523 that covers a central portion of the electrode 503. As illustrated in FIG. 14, the protrusion 523 generally extends a length of the cuff body 501.

As illustrated in FIG. 14 and the sectional view of FIG. 15, the second and third flange members 534, 550 are generally symmetrical in size and shape such that the proximal portions 537 of these respective flange members 534, 550 extend generally outward and upward in opposite directions from base portion 520. Because each flange member 534, 550 includes a generally arcuate concave shape to partially form lumen 540, the distal portions 571 of the respective flange members 534, 550 curve slightly inward such that their respective distal ends 536, 552 are oriented toward a point a convergence. However, in this embodiment, a large gap 539 (identified in FIG. 15) remains between the distal ends 536, 552 of the respective flange members 534, 550.

In one aspect, electrode cuff 500 includes a first flange member 530 having a proximal end 531 that is secured to an outer surface of second flange member 534 with a remaining portion of the first flange member 530 (extending to an unsecured distal end 532) being in releasable contact against a distal portion 571 of the second flange member 534 and against both a distal portion 571 and proximal portion 537 of the third flange member 550. In a manner substantially similar to that described for the embodiment of FIGS. 5-10, access to a lumen 540 is provided via temporarily maneuvering the first flange member 530 away from the third flange member 550 and away from the distal portion 571 of the second flange member 534 (with the proximal end 531 remaining fixed against second flange member 534) to enable placing the cuff 500 onto a target nerve such that the nerve occupies lumen 540. Thereafter, the first flange member 530 is returned to the position shown in FIG. 15, thereby placing the electrode cuff 500 in a fully engaged position or configuration. In this position, the combination of the first flange member 530 with the second flange member 534 and third flange member 550 provides a re-closable opening 539.

In one aspect, in a manner substantially similar to the embodiment of FIG. 5, because the first flange member 530 is slidably movable (and in releasable contact with) relative to the outer surface of the second flange member 534 and the third flange member 550, electrode cuff 500 is automatically adjustable to have an increased diameter of its lumen 540 in response to a larger size nerve or swelling of the nerve enclosed within the lumen 540.

In one aspect, as illustrated in FIG. 14, the electrode cuff 500 includes an array 502 of electrodes 503 spaced apart along a length of the cuff body 501. As best seen in the sectional view of FIG. 15, each electrode 503 forms a generally wishbone cross-sectional shape. It will be understood that in some embodiments, in a manner substantially similar to that previously described in association with FIGS. 3-5, the respective electrodes 503 are electrically connected to lead 80 (FIGS. 3-4) via a coil or other conductive component that extends through a length of the base portion 520. In general terms, the electrodes 503 are formed of a conductive material and are sized and shaped to permit flexible bending of the fingers 504 of the respective electrodes 503 as the respective flange members 534, 550 (in which the electrodes 503 are embedded) are maneuvered to deploy the electrode cuff 500 on a target nerve. In one embodiment, the electrodes 503 are formed of a platinum-iridium material like that of electrodes 501 except with the electrodes 503 having a thickness and width suited to permit limited, flexible bending of the fingers 504 of the electrodes 503 as the respective flange members 534, 550 are maneuvered to deploy electrode cuff 500.

In one aspect, electrode 503 includes a generally U-shaped base portion 508 that defines a recess 509. The respective fingers 504 extend generally outward and upward, from a distal transition region 510 of the base portion 508, in generally opposite directions from each other, as illustrated in FIG. 15. When the electrode 503 is present during molding of the cuff body 501, material fills in the recess 509 of the U-shaped base 508 as the electrode 103 becomes embedded within the base portion 520 of cuff body 501 and embedded within the distal portions 571 of the respective second and third flange members 534, 550. In this arrangement, the electrode 503 is anchored in at least a three-point configuration including a first anchor point at the base portion 520 and two other anchor points at each of the respective distal portions 571 on opposite sides of the cuff 500. In one aspect, this three point anchor configuration forms a triangular shape pattern in which the first anchor point (at base portion 520) is located on an opposite side of lumen 540 from the two other anchor points (at distal portions 571) while the two other anchor points (at distal portions 571 are located on opposite sides of the lumen 540 as well. Accordingly, this three point anchor configuration provides great stability to the embedded position of the electrode 503 within the cuff body 501.

As further illustrated in FIGS. 14-15, the distal portions 571 of second flange member 534 and third flange member 550 are generally tapered such that distal ends 536, 552 are slightly narrower than the wider trunk portions 570 of distal portions 571. Moreover, the generally wider trunk portions 570 are molded to embed distal ends 505 of each finger 504 of an electrode 503 within a recess 572 of the respective second, third flange members 534, 550. In one aspect, by itself, this arrangement acts to prevent delamination or separation of the fingers 504 from the respective second and third flange members 534, 550. However, this arrangement also acts in cooperation with the protrusion 523 and its proximal plug portion 525 (that fills recess 509), which also prevents separation of or delamination of the base 508 of electrode 503 from the base portion 520 of cuff 500. As illustrated in FIG. 15, the portion of each finger 504 of electrode 503 that extends proximally from the trunk portion 570 of each flange member 534, 550 is exposed to lumen 140 for contact against a nerve.

In another aspect, like the embodiment of FIG. 5, the arcuate length of each separate finger 504 of the electrode 503 generally corresponds to a 45 degree arc of lumen 540 (as represented by arc β). With this arrangement, a sufficient surface area of electrode 503 is available for contact with the nerve while the degree or amount of bending of the fingers 504 is sufficiently limited to substantially minimize fatigue failure of portions of the electrode 503.

Figure 16:
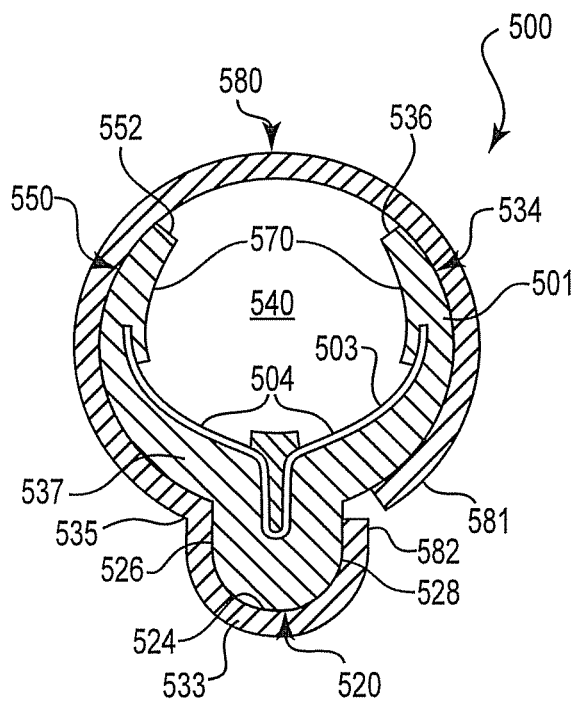
FIG. 16 is a sectional view of the expandable electrode cuff of FIG. 15 with an alternate outer flange member, according to an embodiment of the present disclosure.

As illustrated in FIG. 16, in one embodiment, the electrode cuff 500 of FIGS. 14-15 is modified to provide a first flange member 580 having an increased length (as compared to the length of the first flange member 530) in a manner substantially similar to that previously described for first flange member 330 in association with FIG. 12. Accordingly, the first flange member 580 includes substantially the same features and attributes as the first flange member 330 (FIG. 12), such as including a transition region 535 and a distal cap region 533 that are pre-formed to substantially match a contour of the base portion 520 of the cuff 500 at bottom wall 524 and at a transition between third flange member 552 and the first side wall 126 of base portion 120.

Figure 17:
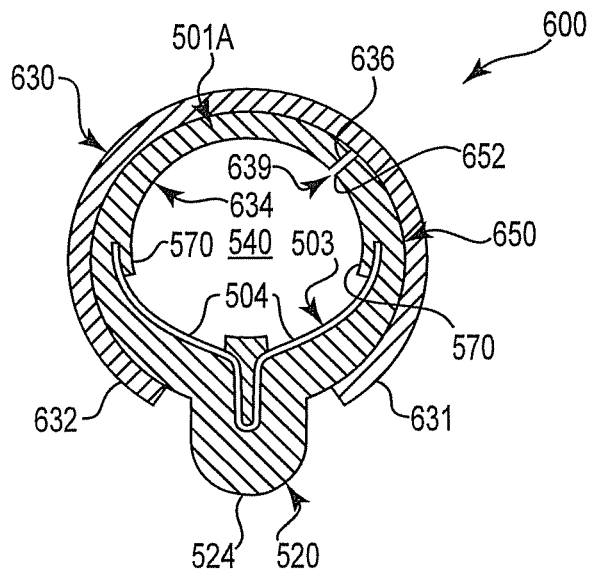
FIG. 17 is a sectional view of an expandable electrode cuff, according to an embodiment of the present disclosure.

FIG. 17 is a sectional view of electrode cuff 600, according to one embodiment of the present disclosure. As illustrated in FIG. 17, electrode cuff 600 comprises substantially the same features and attributes as electrode cuff 500 of FIGS. 14-15, except for including a second flange member 634 having an increased length to substantially reduce the gap in re-closable opening 539 of cuff 500. Accordingly, for electrode cuff 600, the distal ends 636, 652 of the respective second and third flange members 634, 650 are in close proximity to (or releasably contact) each other to form re-closable opening 639. In this arrangement, there is even greater security of maintaining the integrity of lumen 540 about a target nerve because the large gap associated with re-closable opening 539 has been eliminated. In order to deploy electrode cuff 600, after temporarily pulling back the releasable portions of the first flange member 630 from second flange member 634 (with the proximal end 631 remaining fixed against the third flange member 650), the distal end 636 of the second flange member 634 is maneuvered away from the distal end 652 of the third flange member 650 to provide access to lumen 540.

In one aspect, in a manner substantially similar to the previously described embodiments, the electrode cuff 600 is securable about a nerve with the first flange member 630 being slidably movable (and in releasable contact) relative to the second flange member 634 and the second flange member 634 is rotatable away from the third flange member 650 to provide automatic expansion of the lumen 540 while maintaining closure of the lumen 540 and contact of electrode 503 against the nerve, yet without placing undue pressure on the nerve.

Figure 18:
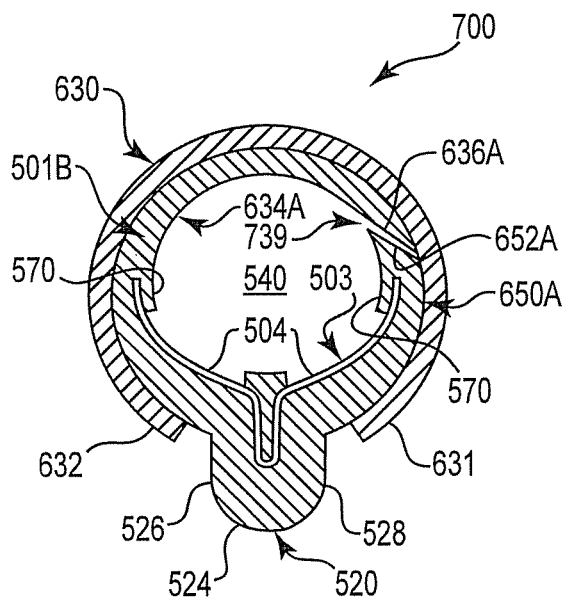
FIG. 18 is a sectional view of an expandable electrode cuff, according to an embodiment of the present disclosure.

FIG. 18 is a sectional view of an electrode cuff 700, according to an embodiment of the present disclosure. As illustrated in FIG. 18, electrode cuff 700 comprises substantially the same features and attributes as electrode cuff 600, except having a modified distal ends 636A, 652A of respective second and third flange members 634A, 650A that are beveled and that releasably mate in a reciprocal manner to form re-closable opening 739. In this arrangement, the reciprocating beveled distal ends 636A, 652A facilitates releasable contact or engagement between those respective distal ends 636A, 652A, which in turn, helps to maintain the electrode cuff 700 in the fully engaged position.

Figure 19:
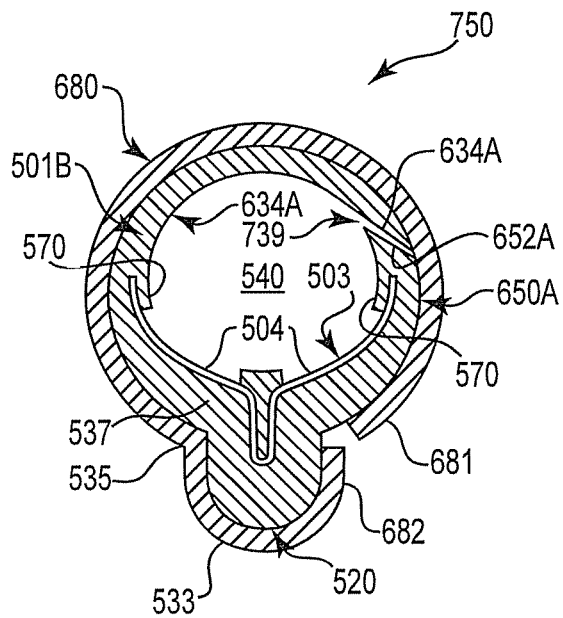
FIG. 19 is a sectional view of an expandable electrode cuff of FIG. 18 with an alternate outer flange member, according to an embodiment of the present disclosure.

FIG. 19 is a sectional view of an electrode cuff 750, according to an embodiment of the present disclosure. As illustrated in FIG. 19, electrode cuff 750 comprises substantially the same features and attributes as electrode cuff 700, except having a first flange member 680 with an increased length compared to first flange member 630. In this arrangement, first flange member 680 comprises substantially the same features and attributes as first flange member 330 (as previously described in association with FIG. 12) and/or first flange member 580 (as previously described in association with FIG. 16). Accordingly, in this instance, the proximal end 681 of first flange member 680 is fixed relative to the third flange member 650A while the remainder of the first flange member 680 is in releasable contact against the second flange member 634A and a majority of the base portion 520, with the distal end 682 of the first flange member 680 being spaced apart, and positioned below, the proximal end 681 of the first flange member 680 on the same side of cuff 750 (i.e., both adjacent to the second side wall 528 of the base portion 520).

Figure 20:
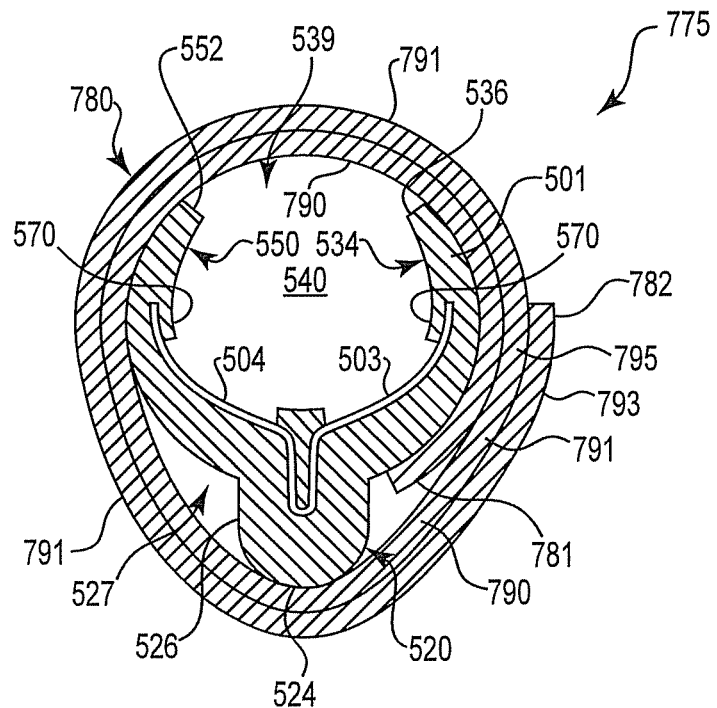
FIG. 20 is a sectional view of an expandable electrode cuff of FIG. 15 with another alternate outer flange member, according to an embodiment of the present disclosure.

FIG. 20 is a sectional view of an expandable electrode cuff 775, according to one embodiment of the present disclosure. In one embodiment, electrode cuff 775 includes substantially the same features and attributes as electrode cuff 500 of FIG. 15, except having a substantially longer first flange member 780 that is wrapped about the cuff body 501 in at least two layers. In particular, with the proximal end 781 of first flange member 780 fixed against second flange member 534, the remaining free portion of first flange member 780 is wrapped about cuff body 501 until the distal end 782 of the first flange member 780 overlaps the position of the proximal end 781. In one embodiment, the first flange member is pre-formed to have a shape substantially similar to that shown in FIG. 20, so that it is biased to generally maintain and/or to return to that shape after temporary manipulation into a different shape.

As illustrated in FIG. 20, a first layer 790 of the first flange member 630 is in releasable contact with the distal portion 570 of the second flange member 534, the third flange member 550, and a bottom wall 524 of the base portion 120. As first flange member 780 makes releasable contact against the proximal end 781 of the first flange member 780. The first flange member 780 extends further distally from that point onward as a second layer 791, overlapping the first layer 790, until the distal end of the 782 of the first flange member 780 forms a partial third layer by again overlapping the proximal end 781 of the first flange member 780. In one embodiment, the first flange member 630 forms at least two complete layers in its position wrapped about a circumference of the cuff body 501 while in other embodiments, more than two or less than two layers can be formed by wrapping the first flange member 780 about the circumference of the cuff body 501 of the electrode cuff 775.

Figure 21:
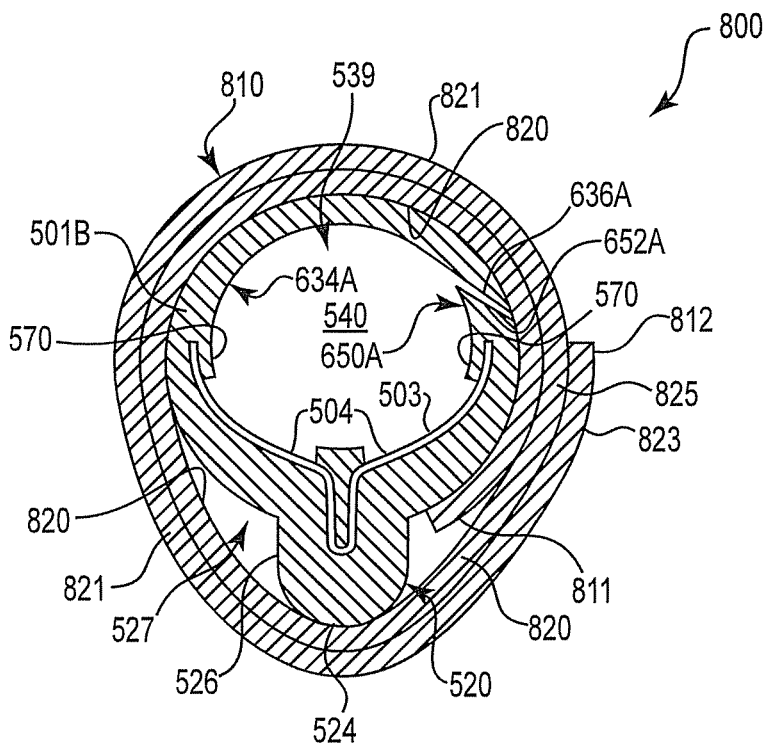
FIG. 21 is a sectional view of an expandable electrode cuff of FIG. 18 with another alternate outer flange member, according to an embodiment of the present disclosure.

FIG. 21 is a sectional view of an expandable electrode cuff 800, according to one embodiment of the present disclosure. In one embodiment, electrode cuff 800 includes substantially the same features and attributes as electrode cuff 700 of FIG. 18, except having a substantially longer first flange member 810 that has substantially the same features and attributes as the first flange member 780 of FIG. 20. With this arrangement, the combination of the reciprocating beveled distal ends 636A, 652A of the respective second and third flange members 634A, 650A and of the multilayer (at least two layers) first flange member 810 wrapped about the cuff body 501B provide a robust mechanism to ensure that the second and third flange members 634A, 652A will maintain capture of the nerve within lumen 140 despite long term placement of the cuff 800 within the body.

Embodiments of the present disclosure ensure long term, robust engagement of an electrode against a nerve. In some embodiments, this robust engagement is accomplished while also accommodating swelling of a nerve or larger sized nerves via automatic expansion and contraction of the lumen defined by the electrode cuff via overlapping, slidably movable flange members comprising the electrode cuff.

While at least one exemplary embodiment has been presented in the foregoing detailed description, it should be appreciated that variations exist. It should also be appreciated that the exemplary embodiment or exemplary embodiments are only examples, and are not intended to limit the scope, applicability, or configuration of the present disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the present disclosure as set forth in the appended claims and the legal equivalents thereof.

We claim:
1. An electrode assembly comprising:
   an elongate cuff body including:
      a base member including a top wall and at least one side wall; and
      a first flange member including a first end and a second end;
      a pair of resilient arcuate-shaped flange members that includes a second flange member and a third flange member,
      wherein the respective second and third flange members each include a proximal portion and a distal end portion, with each respective proximal portion extending from the base outwardly and away from the other respective proximal portion, and
      wherein the respective distal end portions are biased to extend toward each other and to be in releasable contact with each other when the cuff body is in a nerve-engaging position such that the respective second and third flange members define, in combination with the top wall of the base member, a lumen releasably enclosing a nerve and having a substantially re-closable opening, wherein the at least one side wall of the base member protrudes in first orientation away from the lumen, and
      wherein the first end of the first flange member is secured to an outer surface of the third flange member and has a cross-sectional length sufficient to extend from its secured first end to overlap an outer surface of the third flange member and to overlap an outer surface of a portion of the second flange member when the distal end portions of the respective second and third flange members of the cuff body are in the nerve-engaging position, and wherein, when the cuff body is in the nerve-engaging position, at least the second end of the first flange member is in releasable slidable contact against the second flange member and the first flange member also overlaps the substantially re-closable opening between the second and third flange members,
      wherein each of the first, second, and third flange members extend a length of the cuff body; and
   a row of generally rigid electrode elements embedded within the cuff body and spaced apart from each other along the length of the cuff body, wherein in a cross-sectional orientation, each electrode element includes:
      a generally arcuate first portion extending along an inner surface of the second flange member to be exposed at the lumen, wherein the exposed first portion of the electrode element is located generally opposite the substantially re-closable opening of the cuff body; and
      a generally straight second portion extending into the base member away from the lumen at a generally obtuse angle relative to the first portion, wherein the second portion is separate from, and independent of, a lead extending from the base member of the cuff body with the second portion being electrically coupled to the lead.

2. The electrode assembly of claim 1 wherein the first portion of each electrode element has an arcuate length limited to a 45 degree arc of the lumen, and wherein the obtuse angle is about 130 degrees.

3. The electrode assembly of claim 1 wherein the generally arcuate shape of the first portion substantially matches a radius of curvature of the inner surface of second flange member, wherein the first portion includes a distal hook portion extending generally away from the inner surface of the second flange member, and wherein the distal hook portion defines a recess that receives a molded portion of the cuff body to secure the respective electrode element relative to the cuff body.

4. The electrode assembly of claim 1, wherein the cross-sectional length of the first flange member is sufficient for the second end of the first flange member to extend distally beyond the second flange member and at least around a bottom wall of the base member.

5. The electrode assembly of claim 1, wherein the cross-sectional length of the first flange member is sufficient to wrap the first flange member at least two times about the circumference of the cuff body before the second end of the first flange member terminates at a position overlapping the secured first end of the first flange member.

6. The electrode assembly of claim 1 wherein a diameter of the lumen defined by the electrode cuff body is automatically expandable, in response to an increasing diameter of a nerve in the lumen, via rotation of the distal end portion of the second flange member away from the distal end portion of the third flange member and via slidable movement of the first flange member relative to the second flange member with the first flange member having a length sufficient to maintain overlap with the substantially re-closable opening and with a majority of a length of the second flange member during the automatic expansion.

7. The electrode assembly of claim 1, wherein the second flange member has a cross-sectional length substantially greater than a cross-sectional length of the third flange member such that the substantially re-closable opening laterally relative to, and not directly opposite, the base member.

8. The electrode assembly of claim 1 wherein the proximal portions of the respective second and third flange members have a thickness substantially greater than the respective distal end portions, and wherein the thickness of the proximal portion of the second flange member is substantially greater than the thickness of the third flange member such that the relative thicknesses of the second and third flange members are asymmetric.

9. The electrode assembly of claim 8 wherein each respective electrode element is positioned within the proximal portion of the second flange member generally at a region of maximum thickness of the second flange member.

10. The electrode assembly of claim 1 wherein the inner surface of the second flange member in the region of the first portion of the respective electrode elements is recessed relative to remaining portions of the inner surface of the second flange member.

11. The electrode assembly of claim 10 wherein the generally straight second portion of the respective electrode elements extends generally parallel to a cross-sectional longitudinal axis of the base member of the cuff body, wherein each electrode element further comprises a generally straight third portion extending within the base member of the cuff body and outwardly from the second portion in a generally opposite direction from the first portion, and wherein the third portion is generally perpendicular to the second portion.

12. An electrode assembly comprising:
an elongate cuff body including:
a base member including a top wall and at least one side wall;
a first flange member including a first end and an opposite second end; and
a pair of resilient arcuate-shaped flange members including a second flange member and a third flange member, the respective flange members each including a proximal portion that extends from the base member outwardly and away from the other respective proximal portion and a distal end portion that extends toward the other respective distal end portion, wherein the top wall of the base member and the two flange members at least partially define a lumen and wherein the distal end portions define an opening providing access to the lumen, wherein the at least one side wall of the base member protrudes in a first orientation away from the lumen and
wherein each of the first, second, and third flange members extend a length of the cuff body,
wherein the first end of the first flange member is secured to an outer surface of the second flange member and has a cross-sectional length sufficient to extend from the secured first end to overlap, and releasably contact, an outer surface of both the second flange member and the third flange member when at least the distal end portions of the respective second and third flange members are in a nerve-engaging position, wherein in the nerve-engaging position the second end of the first flange member terminates at a location over the third flange member the first flange member overlaps an opening between the distal end portions of the respective second and third flange members; and
a row of resilient electrode elements at least partially embedded within the cuff body and spaced apart from each other along the length of the cuff body, wherein each electrode element includes:
a generally semi-circular first portion extending along an inner surface of the respective flange members and arranged to be exposed at the lumen, wherein the exposed first portion is located generally opposite the opening of the cuff body, wherein the first portion defines a first segment and a second segment that extend outwardly in opposite directions from each other; and
a second portion generally extending outward and away from a midpoint of the first portion, wherein the second portion extends into the base member away from the lumen,
wherein the second portion of each electrode element is separate from, and independent of, a lead extending from the base member of the cuff body with the second portion electrically couplable to the lead.

13. The electrode assembly of claim 12, wherein the second portion of the electrode elements comprises a generally U-shaped portion defining a recess between two spaced apart legs and an apex pointing away from the first portion, wherein each respective leg is connected to and extends from the first portion.

14. The electrode assembly of claim 13, wherein each respective first and second segment is connected to a respective one of the legs of the generally U-shaped second portion, and wherein the second portion extends within the base of the cuff body.

15. The electrode assembly of claim 14, wherein the respective first and second segments, which are generally exposed along the inner surface of the respective second and third flange members, each have a distal end and the respective distal ends are embedded within the distal end portion of the respective second and third flange members.

16. The electrode assembly of claim 14, wherein the cuff body comprises a protrusion that extends into the recess of the generally U-shaped second portion to embed the second portion within the base of the cuff body and that is exposed at the lumen.

17. The electrode assembly of claim 12 wherein the first flange member has a length sufficient for the second end to extend distally beyond the third flange member and at least around a bottom wall of the base of the cuff body.

18. The electrode assembly of claim 12, wherein the first flange member has a length sufficient to wrap the first flange member at least two times about the circumference of the cuff body before the second end terminates at a position overlapping the first end of the first flange member.

19. The electrode assembly of claim 12, wherein, in a fully engaged configuration of the electrode assembly, the first flange member is slidably movable relative to, and in releasable contact with, the second flange member such that at least a portion of the first flange member extends across and covers the substantially re-closable opening.

20. The electrode assembly of claim 19 wherein a diameter of the lumen defined by the electrode cuff body is automatically expandable, in response to an increasing diameter of a nerve in the lumen, via rotation of the distal end portion of the second flange member away from the distal end portion of the third flange member and via slidable movement of the first flange member relative to the second flange member with the first flange member having a length sufficient to maintain overlap with the substantially re-closable opening and with a majority of a length of the second flange member during the automatic expansion.

21. The electrode assembly of claim 20, wherein the distal end portions of the respective second and third flange members are in releasable contact with each other.

22. The electrode assembly of claim 21, wherein the respective distal end portions include reciprocating beveled ends.

23. The electrode assembly of claim 12, wherein the second flange member has a length substantially greater than a length of the third flange member such that the substantially re-closable opening is laterally relative to, and not directly opposite, the base of the cuff body.

24. The electrode assembly of claim 1, wherein the at least one side wall of the base member includes a first side wall and a second side wall, and wherein the base member includes a bottom wall extending between the first and second side walls.

25. The electrode assembly of claim 24, wherein the base member, the second flange member, and the third flange member are formed as a single, unitary molded piece.

26. The electrode assembly of claim 12, wherein the at least one side wall of the base member includes a first side wall and a second side wall, and wherein the base member includes a bottom wall extending between the first and second side walls.

27. The electrode assembly of claim 26, wherein the base member, the second flange member, and the third flange member are formed as a single, unitary molded piece.

28. The electrode assembly of claim 12, wherein the second and third flange members have generally equal cross-sectional lengths.

* * * * *